United States Patent [19]

Cooper et al.

[11] Patent Number: 5,070,205

[45] Date of Patent: Dec. 3, 1991

[54] ALKYL 2-BENZYLIDENE-4-(BENZIMIDAZOL-1-YL)BENZOYLACETATE ESTERS AS INTERMEDIATES

[75] Inventors: Kelvin Cooper, Deal; Michael J. Fray, Canterbury; Kenneth Richardson, Birchington; John Steele, Sandwich, all of England

[73] Assignee: Pfizer Inc., New York, N.Y.

[21] Appl. No.: 517,286

[22] Filed: May 1, 1990

Related U.S. Application Data

[62] Division of Ser. No. 251,413, Sep. 29, 1958, Pat. No. 4,935,430.

[51] Int. Cl.$^5$ .......................................... C07D 235/04
[52] U.S. Cl. .................................................. 548/333
[58] Field of Search ................................ 548/325, 333

[56] References Cited

U.S. PATENT DOCUMENTS

| | | | |
|---|---|---|---|
| 3,971,791 | 7/1976 | Meyer | 546/256 |
| 4,285,955 | 8/1981 | Wehinger et al. | 546/257 |
| 4,414,213 | 11/1983 | Poindexter et al. | 546/256 |
| 4,788,205 | 11/1988 | Cooper et al. | 546/256 |
| 4,820,842 | 4/1989 | Anderson et al. | 546/255 |

*Primary Examiner*—Jane T. Fan
*Attorney, Agent, or Firm*—Peter C. Richardson; J. Trevor Lumb; James M. McManus

[57] ABSTRACT

Intermediates useful in the synthesis of dihydropyridine platelet activating factor antagonists of the formula

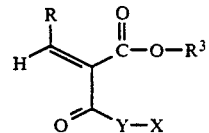

where R is phenyl or substituted phenyl; $R^3$ is lower alkyl; Y is 1,4-phenylene and X is a benzimidazol-1-yl.

1 Claim, No Drawings

ALKYL 2-BENZYLIDENE-4-(BENZIMIDAZOL-1-YL) BENZOYLACETATE ESTERS AS INTERMEDIATES

This is a divisional application of application Ser. No. 251,413 filed Sept. 29, 1988, now U.S. Pat. No. 4,935,430, issued June 19, 1990.

BACKGROUND OF THE INVENTION

This invention relates to dihydropyridines, specifically to certain 4-aryl-5-carbamoyl-1,4-dihydropyridines which are useful in the treatment of allergic and inflammatory conditions in humans and animals.

A number of 1,4-dihydropyridines have been previously described as antiischaemic and antihypertensive agents. These compounds are able to inhibit the movement of calcium into cells and are thus active in the treatment or prevention of a variety of cardiac conditions or as antihypertensive agents. (See for example EP-A-100189.) However the compounds of the present invention are potent and selective antagonists of platelet activating factor and as such they have clinical utility in a quite different area, namely for treating allergic and inflammatory conditions such as asthma and arthritis respectively.

Platelet activating factor (PAF) 1-O-alkyl-2-acetyl-sn-glyceryl-3-phosphorylcholine) is an ether phospholipid whose structure was first elucidated in 1979. It is produced by, released from and interacts with many pro-inflammatory cells, platelets and the kidney. In addition to potent platelet aggregating activity, PAF exhibits a wide spectrum of biological activities elicited either directly or via the release of other powerful mediators such as thromboxane $A_2$ or the leukotrienes. In vitro, PAF stimulates the movement and aggregation of neutrophils and the release therefrom of tissue-damaging enzymes and oxygen radicals. These activities contribute to actions of PAF in vivo consistent with it playing a significant role in inflammatory and allergic responses. Thus, intradermal PAF has been shown to induce an inflammatory response, with associated pain, accumulation of inflammatory cells and increased vascular permeability, comparable with the allergic skin reaction following exposure to allergen. Similarly, both the acute bronchoconstriction and chronic inflammatory reactions elicited by allergens in asthma can be mimicked by intratracheal administration of PAF. Accordingly agents which antagonise the actions of PAF and, consequently also prevent mediator release by PAF, will have clinical utility in the treatment of a variety of allergic, inflammatory and hypersecretory conditions such as asthma, arthritis, rhinitis, bronchitis and urticaria.

In addition to the above, PAF has been implicated as being involved in a number of other medical conditions. Thus in circulatory shock, which is characterised by systemic hypotension, pulmonary hypertension and increased lung vascular permeability, the symptoms can be mimicked by infusion of PAF. This coupled with evidence showing that circulating PAF levels are increased by endotoxin infusion indicate that PAF is a prime mediator in certain forms of shock. Intravenous infusion of PAF at doses of 20-200 pmol $kg^{-1}$ $min^{-1}$ into rats results in the formation of extensive haemorrhagic erosions in the gastric mucosa and thus PAF is the most potent gastric ulcerogen yet described whose endogenous release may underlie or contribute to certain forms of gastric ulceration. Psoriasis is an inflammatory and proliferative disease characterised by skin lesions. PAF is pro-inflammatory and has been isolated from lesioned scale of psoriatic patients indicating PAF has a role in the disease of psoriasis. And finally, increasing evidence supports a potential pathophysiological role for PAF in cardiovascular disease. Thus recent studies in angina patients show PAF is released during atrial pacing. Intracoronary injection of PAF in pigs induces a prolonged decrease in coronary flow and, in guinea pig hearts, it induces regional shunting and ischaemia. In addition PAF has been shown to initiate thrombus formation in a mesenteric artery preparation, both when administered exogenously and when released endogenously. More recently PAF has been shown to play a role in brain ischaemia induced in animal models of stroke.

Thus the compounds of the invention, by virtue of their ability to antagonise the actions of PAF, are likely to be of value in the treatment of any of the above conditions.

Our published patent applications EP-A-258033 and EP-A-266989 disclose 4-aryl-5-carbamoyl-1,4-dihydropyridines as PAF antagonists. These correspond to U.S. Pat. Nos. 4,788,205 and 4,801,598.

SUMMARY OF THE INVENTION

According to the present invention there are provided compounds of formula (I):

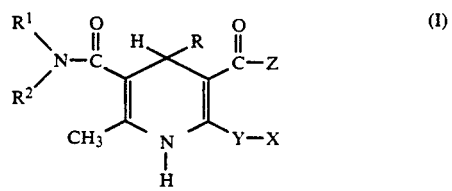

wherein
R is phenyl or phenyl substituted by one or more substituents independently selected from nitro, halo, $C_1$–$C_4$ alkyl, $C_1$–$C_4$ alkoxy, aryl($C_1$–$C_4$)alkoxy, fluoro($C_1$–$C_4$)alkoxy, $C_1$–$C_4$ alkylthio, $C_1$–$C_4$ alkylsulphonyl, hydroxy, trifluoromethyl and cyano, or is phenyl fused to a dioxolane ring;
$R^1$ and $R^2$ are each independently H or $C_1$–$C_6$ alkyl, or $R^1$ and $R^2$ together complete a pyrrolidinyl, piperidino, morpholino, piperazinyl, N-($C_1$–$C_4$ alkyl)piperazinyl or N-($C_2$–$C_4$ alkanoyl)-piperazinyl group;
$R^2$ is H or $C_1$–$C_4$ alkyl and $R^1$ is CN, $C_3$–$C_7$ cycloalkyl, aryl, heteroaryl or a $C_1$–$C_4$ alkyl group, said $C_1$–$C_4$ alkyl group of $R^1$ being substituted by one or more substituents each independently selected from $C_3$–$C_7$ cycloalkyl, $C_1$–$C_4$ alkoxycarbonyl, aryl and heteroaryl; Z is selected from $C_1$–$C_6$ alkoxy, aryl($C_1$–$C_4$)alkoxy, hydroxy, and —$NR^4R^5$ wherein each of $R^4$ and $R^5$ is independently H or $C_1$–$C_6$ alkyl, or $R^4$ and $R^5$ together complete a pyrrolidinyl, piperidino, morpholino, piperazinyl or N-($C_1$–$C_4$ alkyl)piperazinyl group; Y is 1,4 phenylene or pyridine-2,5-diyl; and X is a 5 or 6 membered aromatic heterocyclic group containing one or more nitrogen atoms in its ring; which ring may be optionally fused to a benzene ring or to a further 5- or 6-membered aromatic heterocyclic ring containing one or more nitrogen atoms, at least one of said heterocyclic rings optionally also containing an oxygen or sulphur atom and being optionally substituted with one or more substituents independently selected from $C_1-C_4$ alkyl, $C_1-C_4$ alkoxy, halo, $CF_3$ and CN;
and their pharmaceutically acceptable salts.

According to one aspect of the invention, there are provided compounds of formula (Ia):

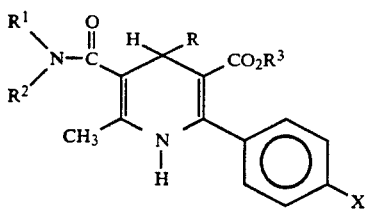

(Ia)

wherein
R is phenyl or phenyl substituted by one or more substituents selected from nitro, halo, $C_1-C_4$ alkyl, $C_1-C_4$ alkoxy, aryl $(C_1-C_4)$alkoxy, $C_1-C_4$ alkylthio, $C_1-C_4$ alkylsulphonyl, hydroxy, trifluoromethyl and cyano;

$R^1$ and $R^2$ are each independently H or $C_1-C_6$ alkyl, or the two groups may be joined together to form a pyrrolidinyl, piperidino, morpholino, piperazinyl N-($C_1-C_4$ alkyl)piperazinyl or N-($C_2-C_4$ alkanoyl)-piperazinyl group; or $R^2$ is H or $C_1-C_4$ alkyl and $R^1$ is CN, $C_3-C_7$ cycloalkyl, aryl, heteroaryl or a $C_1-C_4$ alkyl group substituted by one or more substituents selected from $C_3-C_7$ cycloalkyl, $C_1-C_4$ alkoxycarbonyl, aryl or heteroaryl; $R^3$ is $C_1-C_6$ alkyl or aryl $(C_1-C_4)$alkyl;

X is a 5 or 6 membered aromatic heterocyclic group containing one or more nitrogen atoms; which may be optionally fused to a benzene ring or to a further 6 membered aromatic heterocyclic group containing one or more nitrogen atoms; and which may be optionally substituted with one or more substituents selected from $C_1-C_4$ alkyl, $C_1-C_4$ alkoxy, halo, $CF_3$ and CN; and their pharmaceutically acceptable salts.

According to another aspect of the invention, there are provided compounds of formula (Ia) above wherein
R is phenyl or phenyl substituted by one or more substituents selected from nitro, halo, $C_1-C_4$ alkyl, $C_1-C_4$ alkoxy, aryl $(C_1-C_4)$alkoxy, $C_1-C_4$ alkylthio, $C_1-C_4$ alkylsulphonyl, hydroxy, trifluoromethyl and cyano;

$R^1$ and $R^2$ are each independently H or $C_1-C_6$ alkyl, or the two groups may be joined together to form a pyrrolidinyl, piperidino, morpholino, piperazinyl, N-($C_1-C_4$ alkyl)piperazinyl or N-($C_2-C_4$ alkanoyl)-piperazinyl group; or $R^2$ is H or $C_1-C_4$ alkyl and $R^1$ is CN, $C_3-C_7$ cycloalkyl, aryl, heteroaryl or a $C_1-C_4$ alkyl group substituted by one or more substituents selected from $C_3-C_7$ cycloalkyl, $C_1-C_4$ alkoxycarbonyl, aryl or heteroaryl;

$R^3$ is $C_1-C_6$ alkyl or aryl$(C_1-C_4)$alkyl;

X is a 5- or 6-membered aromatic heterocyclic group containing one or more nitrogen atoms in its ring; which ring may be optionally fused to benzene ring or to a further 5- or 6-membered aromatic heterocyclic ring containing one or more nitrogen atoms, at least one of said heterocyclic rings also containing an oxygen or sulphur atom; and which may be optionally substituted with one or more substituents selected from $C_1-C_4$ alkyl, $C_1-C_4$ alkoxy, halo, $CF_3$ and CN; and their pharmaceutically acceptable salts.

According to another aspect of the invention, there are provided compounds of formula (Ib):

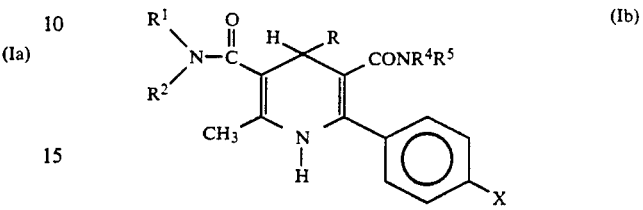

(Ib)

in which R, $R^1$, $R^2$ and X are as defined above; and each of $R^4$ and $R^5$ is independently H or $C_1-C_6$ alkyl, or the two groups may be joined together to form with the nitrogen atom to which they are attached a pyrrolidinyl, piperidino, morpholino, piperazinyl or N-($C_1-C_4$ alkyl)piperazinyl group.

In the definitions given herein, the term halo means fluoro, chloro, bromo or iodo. Alkyl and alkoxy groups of 3 or more carbon atoms, and $C_4$ alkanoyl groups, may be straight or branched-chain.

Aryl used in the definition of $R^1$ and Z means phenyl or phenyl substituted by one or more (preferably 1 or 2) substituents each independently selected from halo, trifluoromethyl, $C_1-C_4$ alkyl, hydroxy, $C_1-C_4$ alkoxy, ($C_1-C_4$ alkoxy)carbonyl, sulphamoyl and CN.

Heteroaryl used in the definition of $R^1$ means a. 5- or 6-membered aromatic heterocyclic group containing one or more heteroatoms independently each selected from N, O and S and which may optionally be fused to a benzene ring and which may optionally be substituted in at least one of the heterocyclic and fused benzene rings by one or more substituents independently selected from $C_1-C_4$ alkyl, $C_1-C_4$ alkoxy and halo.

Examples of suitable heteroaryl groups include pyridyl, thiazolyl, thiadiazolyl, oxazolyl and imidazolyl, any of which may optionally be benzofused and optionally substituted in the heterocyclic and fused benzene rings by $C_1-C_4$ alkyl, $C_1-C_4$ alkoxy or halo. Thus particular examples of $R^1$ as heteroaryl include pyrid-2-yl, 4- and 6-methylpyrid-2-yl, thiazol-2-yl, 4- and 5-methylthiazol-2-yl, 5-methylthiadiazol-2-yl, 5-methyloxadiazol-3-yl, 5-methylisoxazol-3-yl, benzothiazol-2-yl and 5-ethoxybenzothiazol-2-yl, and 1-methylimidazol-2-yl.

Preferably $R^2$ is H and $R^1$ is H, $C_1-C_4$ alkyl, pyridyl (most preferably 2-pyridyl), thiazolyl (most preferably 2-thiazolyl) or 1-(phenyl)ethyl.

In a preferred aspect of the invention Z is ethoxy, methoxy, or benzyloxy ring-substituted by halo (i.e. $R^3$ is ethyl, methyl or benzyl ring-substituted by halo). R is preferably 2-chlorophenyl, 2-trifluoromethoxyphenyl, 2,4-difluorophenyl, 4-cyanophenyl or 1,3-benzodioxol-4-yl.

X may be a 1,2,4-triazolyl group optionally substituted with one or two $C_1-C_4$ alkyl groups, or an imidazolyl group optionally substituted with up to three $C_1-C_4$ alkyl groups or optionally substituted with a $C_1-C_4$ alkyl or $CF_3$ group and fused to a benzene or pyridine or pyrimidine ring which may be substituted with at least one $C_1-C_4$ alkyl or $C_1-C_4$ alkoxy group. X may alternatively be a pyridyl group optionally substituted with from one to three $C_1$–$C_4$ alkyl or $CF_3$ groups.

Alternatively, X may be an oxazolyl or thiazolyl group optionally substituted with up to two $C_1$–$C_4$ alkyl groups, or an imidazolyl group optionally substituted with a $C_1$–$C_4$ alkyl or $CF_3$ group and fused to an oxazolyl or thiazolyl ring.

X is more preferably 2-methylimidazo[4,5-c]pyrid-1-yl, imidazol-1-yl, benzimidazol-1-yl, 2-methylbenzimidazol-1-yl, 3,5-dimethyl-1,2,4-triazol-4-yl, 2-trifluoromethylimidazo[4,5-c]pyrid-1-yl, 2-butylimidazo[4,5-c]pyrid-1-yl, 2-methylimidazo[4,5-b]pyrid-3-yl, 2-methylimidazo[1,2-a]pyrid-3-yl, 2-ethylimidazo[4,5-c]pyrid-1-yl, 7-methoxy-2-methylimidazo[4,5-d]pyrimid-3-yl, 2-methylimidazo[4,5-c]pyrid-3-yl, 2,4,6-trimethylimidazo[4,5-c]pyrid-1-yl, 2,4-dimethylimidazol-1-yl, 2-methylimidazol-1-yl, 2,4,5-trimethylimidazol-1-yl, 4-methylimidazol-1-yl, 2-methylpyrid-3-yl, 2,6-dimethylpyrid-3-yl, 3,5-dimethyl-1,2,4-triazol-1-yl, 4-methyloxazol-5-yl, 2,4-dimethylthiazol-5-yl, 6-methylimidazo[1,2-b]thiazol-5-yl, or 4-methylthiazol-5-yl.

Particularly preferred individual compounds are 4-(2-chlorophenyl)-1,4-dihydro-3-ethoxycarbonyl-6-methyl-2-[4-(2-methylimidazo[4,5-c]pyrid-1-yl)phenyl]-5-[N-(2-pyridyl)carbamoyl]pyridine; 4-(2-chlorophenyl)-1,4-dihydro-3-ethoxycarbonyl-6-methyl-2-[4-(2-methylimidazo[1,2-a]pyrid-3-yl)phenyl]-5-[N-(2-pyridyl)carbamoyl]pyridine; 4-(2-chlorophenyl)-1,4-dihydro-3-ethoxycarbonyl-6-methyl-2-[4-(2,4,6-trimethylimidazo[4,5-c]pyrid-1-yl)phenyl]-5-[N-(2-pyridyl)carbamoyl]pyridine and 4-(2-chlorophenyl)-1,4-dihydro-3-ethoxycarbonyl-6-methyl-2-[2-(2-methylimidazo[4,5-c]pyrid-1-yl)pyrid-5-yl]-5-[N-(2-pyridyl)carbamoyl]pyridine.

Other particularly preferred individual compounds are those whose preparation is also described hereafter in the Examples.

The compounds of formula (I) contain at least one asymmetric centre and will therefore exist as one or more pairs of enantiomers, and such pairs of individual isomers may be separable by physical methods, e.g. by fractional crystallisation or chromatography of the parent compounds or of a suitable salt or derivative thereof. Alternatively, particular isomers may be prepared using the corresponding optical isomers of the precursors used in preparation of compounds of the invention. The invention includes all the enantiomers of the compounds of formula (I) whethere separated or not.

The pharmaceutically acceptable acid addition salts of the compounds of formula (I) are those formed from acids which form non-toxic acid addition salts, for example the hydrochloride, hydrobromide, sulphate or bisulphate, phosphate or acid phosphate, acetate, citrate, fumarate, gluconate, lactate, maleate, succinate, tartrate, methanesulphonate, benzenesulphonate and p-toluenesulphonate.

DETAILED DESCRIPTION OF THE INVENTION

Compounds of the invention in which Z is $C_1$–$C_6$ alkoxy or aryl($C_1$–$C_4$)alkoxy may be prepared via the Hantzsch synthesis according to the following reaction scheme:

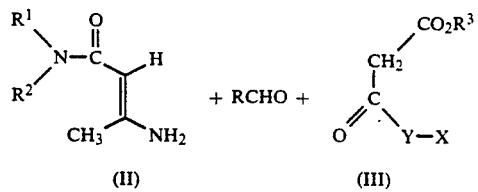

wherein R, $R^1$, $R^2$, $R^3$, Y and X are as previously defined.

In a typical procedure, the aminocrotonamide (II), the ketoester (III) and aldehyde are heated in a suitable organic solvent, e.g. a $C_1$–$C_4$ alkanol such as ethanol, at 60°–130° C., preferably under reflux, until the reaction is essentially complete, typically in 24 hours or less. Optionally a small amount of a lower alkanoic acid such as acetic acid is present to neutralise the solution. The product of the formula (I) can then be isolated and purified by conventional procedures, for example by partition, recrystallisation or by chromatography.

In an alternative procedure, the keto-ester of formula (III) and the aldehyde are reacted together, typically by stirring a slight excess of ketoester with the aldehyde at room temperature for 48 hours in a suitable organic solvent, e.g. isopropyl alcohol containing piperidine as a catalyst, to give an intermediate compound of formula (IV):

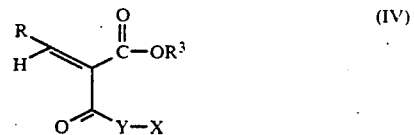

If desired, the intermediate compound may be separated, for example by evaporating the reaction mixture to produce an oil, triturating the oil with water and purifying the product by filtration and recrystallisation from ethyl acetate. The compound of formula (IV) may then be reacted with amino-crotonamide (II), for example by heating the compounds together in an alcoholic solvent at 60°–130° C. and preferably under reflux, to produce the compound of formula (I). The compound so produced may be separated by conventional methods.

The keto esters of formula (III) are either known compounds or can be prepared by the following methods:

(i) The keto esters of formula (III) may be prepared by a Blaise reaction based on a modification of the literature method according to S. M. Hannick, Y. Kishi, *J. Org. Chem.*, 1983, 48, 3833 via the following reaction sequence:

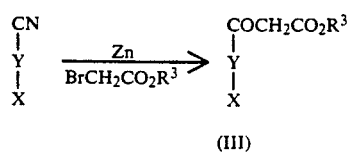

The cyano compound is added to a suspension of zinc dust and the appropriate bromoacetate in an inert solvent, such as tetrahydrofuran, under nitrogen. Further amounts of the appropriate bromoacetate are added, under reflux, followed by the addition of aqueous potassium carbonate after cooling. After filtration the filtrate is hydrolysed by refluxing for several hours with dilute hydrochloric acid or by stirring with 20% aqueous trifluoroacetic acid in a solvent such as dichloromethane.

The reaction mixture is then neutralised and the keto ester of formula (III) isolated and purified by conventional procedures, for example by partition, recrystallisation or chromatography.

The cyano compounds are either known compounds or may be prepared by known methods in accordance with literature precedents as illustrated herein.

(ii) An alternative method for preparing certain keto esters of formula (III) is by the Goldberg and Claisen ester condensation according to the following reaction sequence:

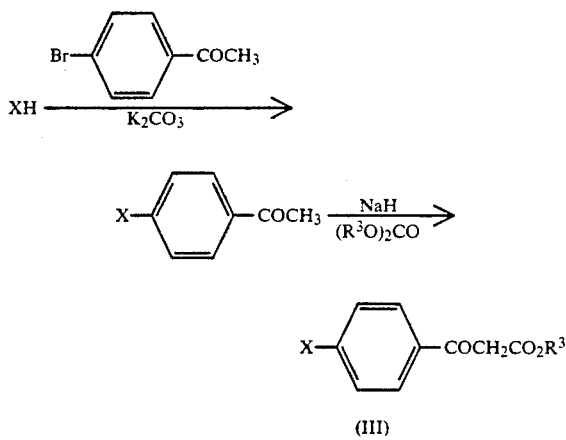

The p-bromoacetophenone may be replaced by the corresponding fluorine, chlorine or iodine compound and a copper/cuprous bromide catalyst may be added in the first stage of this sequence.

In a typical procedure, a mixture of a compound XH, p-bromoacetophenone, copper bronze, cuprous bromide and anhydrous potassium carbonate in a solvent such as dry N-methylpyrrolidinone is heated under an inert atmosphere for up to 8 hours. The solvent is then removed and the intermediate ketone isolated and purified by conventional procedures.

The intermediate ketone is added to a suspension of sodium hydride in dry solvent, such as tetrahydrofuran, under nitrogen. The appropriate dialkylcarbonate is added and the resultant mixture refluxed for about 18 hours. Alternatively, the dialkylcarbonate may itself be used as the solvent. The keto ester of formula (III) is isolated and purified by conventional procedures.

The amino-crotonamides (II) are either known compounds or can be prepared by conventional procedures, for example from the ketoamide by reaction with ammonia.

Likewise the aldehydes RCHO are either known or can be prepared by known methods in accordance with literature precedents.

In an alternative method of making compounds of formula (I) in which Z is $C_1$-$C_6$ alkoxy or aryl($C_1$-$C_4$)alkoxy, a carboxylic acid of formula (V) is reacted with ammonia or an amine of formula $NHR^1R^2$, wherein R, $R^1$, $R^2$, $R^3$, X and Y are as defined above:

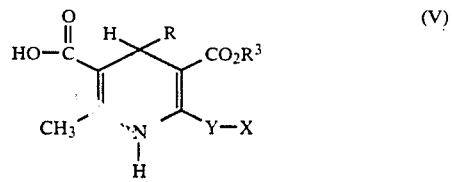

In a typical procedure the compound of formula (V) is stirred in dichloromethane containing 2,4,6-tri-isopropylbenzenesulphonyl chloride and 4-(N,N-dimethylamino)pyridine at room temperature and the ammonia or amine is then added. The compound of formula (I) obtained is separated by evaporation of the solution, extraction with aqueous acid, neutralisation of the aqueous phase, extraction of the aqueous phase with dichloromethane and flash chromatography of the extract.

The compound of formula (V) may be obtained by hydrolysis of a compound of formula (VI):

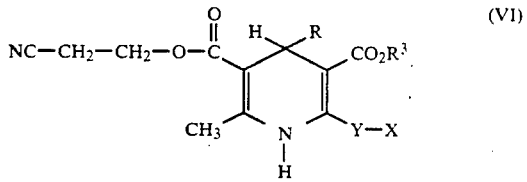

The hydrolysis may be performed using aqueous sodium hydroxide and a solvent such as dioxane. The compound of formula (VI) may be prepared by a Hantzsch synthesis using the appropriate keto-ester of formula (III), an aldehyde of formula RCHO and 2-cyanoethyl 3-aminobut-2-enoate.

Preparation of the compound of formula (I) using the compound of formula (VI) as described above allows particular optical isomers of compounds of formula (I) to be obtained. The Hantzsch synthesis will produce a mixture of (+) and (−) isomers of compound (VI) but these may be resolved by formation of a salt. In one procedure the unresolved cyanoethyl ester of formula (VI) is dissolved in a hot solution of an alcoholic solvent such as methanol and treated with an optical isomer of 4-(2,4-dichlorophenyl)-5,5-dimethyl-2-hydroxy-1,3,2-dioxaphosphorinane-2-oxide to form a solution of diastereomeric salts (a method described by W. den Hoeve, H. Wynberg, J. Org. Chem, (1985) 50, 4508). Fractional recrystallisation of the salt produces one diastereocyanoethyl ester salt. The free cyanoethyl ester may be recovered by treatment of this salt with a base such as sodium carbonate.

The resolved cyanoethylesters may be converted to the resolved compounds of formula (I) by the procedure described above.

Compounds of formula (I) in which Z is OH or —$NR^4R^5$ are conveniently obtained by means of simple chemical transformation reactions. Thus for example compounds of formula (I) wherein Z is benzyloxy may be subjected to a conventional catalytic hydrogenation to yield the corresponding compounds wherein Z is OH. The acid product, or a derivative thereof such as an acid chloride, may be converted to the corresponding compound in which Z is —$NR^4R^5$ by reaction with ammonia or an amine $R^4R^5NH$ under appropriate conditions. Suitable reagents and conditions for these transformations will be well known to those skilled in the art.

The activity of the compounds of the invention is shown by their ability to inhibit the platelet aggregating activity of PAF in vitro. Testing is performed as follows:

Blood samples are taken from either rabbit or man into 0.1 vol disodium ethylenediamine tetraacetic acid buffer and the samples centrifuged for 15 minutes to obtain platelet rich plasma. The plasma is further centrifuged to give a platelet pellet which is washed with a buffer solution (4 mM $KH_2PO_4$, 6 mM $Na_2HPO_4$, 100 mM NaCl, 0.1% glucose and 0.1% bovine serum albumin, pH 7.25) and finally resuspended in buffer solution to a concentration of $2 \times 10^8$ platelets/ml. A sample (0.5 ml) is pre-incubated for two minutes at 37° C. in a Paton aggregometer with stirring, either with vehicle alone, or with vehicle containing the particular compound under test. PAF is added at a sufficient concentration to give a maximum aggregating response in the absence of test compound ($10^{-8}$ to $10^{-9}$ molar), and the platelet aggregation is measured by following the increase in light transmission of the solution. The experiment is repeated in the presence of test compound at a range of concentrations and the concentration of compound required to reduce the response to 50% of its maximum value is recorded as the $IC_{50}$ value.

The activity of the compounds of formula (I) is also demonstrated in vivo by their ability to protect mice from the lethal effect of an injection of PAF. A mixture of PAF (50 μg/kg) and DL-propranolol (5 mg/kg) in 0.9% w/v sodium chloride is injected (0.2 ml) via a tail vein into mice. The compounds under test are either injected into the tail vein immediately prior to the PAF/propranolol injection or administered orally by gavage two hours earlier. The compounds are tested at several doses in groups of 5 mice and the dose which reduces mortality to 50% is recorded as the $PD_{50}$ value.

The compounds are also tested for their ability to reduce PAF-induced bronchoconstriction in anaesthetised guinea pigs. In this test airways resistance and dynamic lung compliance are calculated from recordings of airflow and transpleural pressure and calculation of tidal volume. The bronchoconstriction induced by PAF (100 ng/kg) is determined. One hour after the initial dose of PAF the compound under test is administered and the test repeated. The ability of the compound to reduce the bronchoconstrictor effect of PAF is recorded as a ratio.

For therapeutic use the compounds of the formula (I) will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For administration to man in the curative or prophylactic treatment of allergic bronchial conditions and arthritis, oral dosages of the compounds will generally be in the range of from 2-1000 mg daily for an average adult patient (70 kg). Thus for a typical adult patient, individual tablets or capsules contain from 1 to 500 mg of active compound, in a suitable pharmaceutically acceptable vehicle or carrier. Dosages for intravenous administration would typically be within the range 1 to 10 mg per single dose as required. For the treatment of allergic and bronchial hyper-reactive conditions, inhalation via a nebuliser or aerosol may be the preferred route of drug administration. Dose levels by this route would be within the range 0.1 to 50 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

Thus in a further aspect the invention provides a pharmaceutical composition comprising a compound of the formula (I), or a pharmaceutically acceptable salt thereof, together with a pharmaceutically acceptable diluent or carrier.

The invention also includes a compound of the formula (I), or a pharmaceutically acceptable salt thereof, for use in medicine, in particular in the treatment of allergic and inflammatory conditions in a human being.

The preparation of the compounds of formula (I) is further illustrated by the following Examples.

EXAMPLE 1

4-(2-Chlorophenyl)-1,4-dihydro-3-ethoxycarbonyl-6-methyl-2-[4-(2-methylimidazo[4,5-c]pyrid-1-yl)phenyl]-5-[N-(2-pyridyl)carbamoyl]pyridine A mixture of ethyl 4'-(2-methylimidazo[4,5-c]pyrid-1-yl)benzoylacetate (475 mg, 1.47 mmol), N-(2-pyridyl)-3-aminocrotonamide (260 mg, 1.47 mmol) and 2-chlorobenzaldehyde (207 mg, 1.47 mmol) in absolute ethanol was heated under nitrogen at reflux for 8 hours. The solution was allowed to cool, and the solvent was removed under reduced pressure. The residue was purified by flash chromatography (gradient elution with 5% diethylamine/ethyl acetate and methanol) and the fractions containing the product were concentrated. The solid product was further purified by trituration with diethyl ether/ethyl acetate, followed by filtration and drying of the solid in vacuo to give the title compound (280 mg, 31%), m.p. 226°–228° C.

Analysis %: Found: C, 66.86; H, 4.76; N, 13.72. Calculated (for hemihydrate): C, 66.50; H, 4.92; N, 13.68.

EXAMPLES 2–28

Further compounds of the general formula (Ia) were prepared in accordance with the method of Example 1 using the appropriate aldehyde, the appropriate 4'-substituted benzoylacetic ester and N-substituted crotonamide:

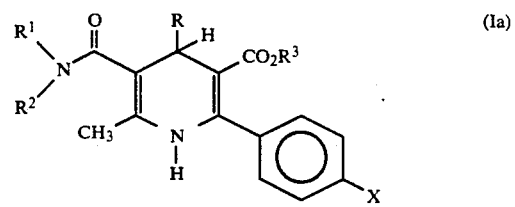

(Ia)

The compounds are shown in Table 1.

TABLE 1

| Example No. | R | R¹ | R² | R³ | X | m.p. °C. | Yield % | Analysis % (Theoretical in brackets) | | |
|---|---|---|---|---|---|---|---|---|---|---|
| | | | | | | | | C | H | N |
| 2 | 2-chloro-6-methylphenyl | t-Bu | H | Et | 2-methyl-imidazo[4,5-b]pyridinyl | 156–159 | 15 | 67.82 (67.86) | 5.80 (5.87) | 11.72 (11.99) |
| 3 | 2-chloro-6-methylphenyl | 2-thiazolyl | H | Me | imidazolyl | 235–238 (dec.) | 16 | 59.59 (59.53)# | 4.5 (4.65) | 11.83 (11.96) |
| 4 | 2-chloro-6-methylphenyl | 2-pyridyl | H | Et | benzimidazolyl | 208–211 (dec.) | 7 | 68.39 (68.16)* | 4.67 (4.88) | 11.61 (11.69) |
| 5 | 2-chloro-6-methylphenyl | t-Bu | H | Et | 2-methylbenzimidazolyl | 157–159 | 25 | 69.80 (70.03) | 5.97 (6.05) | 9.50 (9.61) |
| 6 | 2-chloro-6-methylphenyl | 2-pyridyl | H | Et | 3,5,6-trimethyl-1,2,4-triazinyl | 188–189 | 43 | 64.29 (64.41)* | 5.00 (5.23) | 14.14 (14.54) |

TABLE 1-continued

| Example No. | R | R¹ | R² | R³ | X | m.p. °C. | Yield % | Analysis % (Theoretical in brackets) C | H | N |
|---|---|---|---|---|---|---|---|---|---|---|
| 7 | 2-Cl-phenyl | t-Bu | H | Et | (structure: -N=C(CH₃)-N=C(CH₃)-, CH₃ groups) | 161-162 | 20 | 64.84 (64.68*) | 6.07 6.33 | 12.60 12.57 |
| 8 | 2-Cl-phenyl | 2-methylpyridyl | H | Et | (structure with CF₃, fused pyridine) | 135-138 | 7 | (see below for NMR data)** | | |
| 9 | 2-Cl-phenyl | 2-methylpyridyl | H | Et | (structure with n-Bu, fused pyridine) | 202-204 | 18 | 67.68 (67.55#) | 5.56 5.71 | 12.31 12.52 |
| 10 | 2-Cl-phenyl | 2-methylpyridyl | H | Et | (structure with CH₃, fused pyridine with N) | 197-199 | 10 | 66.50 (66.49*) | 4.89 4.92 | 13.63 13.69 |
| 11 | 2-Cl-phenyl | 2-methylpyridyl | H | Et | (structure with Me, imidazo-pyridine) | 190-191 | 15 | 68.00 (68.56Δ) | 5.00 5.14 | 11.40 11.34 |

TABLE 1-continued
| Example No. | R | R¹ | R² | R³ | X | m.p. °C. | Yield % | Analysis % (Theoretical in brackets) C | H | N |
|---|---|---|---|---|---|---|---|---|---|---|
| 12 | 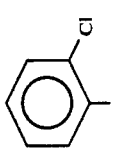 | 2-pyridyl | H | Et | 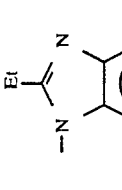 | 255-257 | 13 | 67.20 (66.92) | 5.00 5.13 | 13.09 13.3)* |
| 13 | 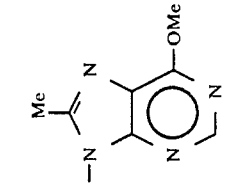 | 2-pyridyl | H | Et | 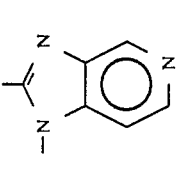 | 220-222 | 27 | 63.30 (63.29) | 4.74 4.84 | 15.09 15.20)* |
| 14 | 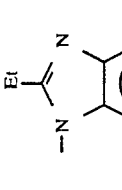 | H | H | Et | 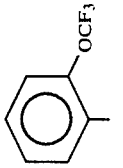 | 200-202 | 14 | 63.64 (63.78) | 5.03 5.16 | 12.41 12.82)+ |
| 15 | 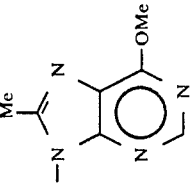 | 2-pyridyl | H | Et | 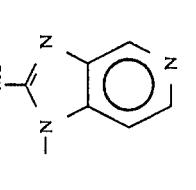 | 235-238 | 4 | 62.63 (62.49) | 4.53 4.65 | 12.29 12.49)+ |

TABLE 1-continued
| Example No. | R | R¹ | R² | R³ | X | m.p. °C. | Yield % | Analysis % (Theoretical in brackets) C | H | N |
|---|---|---|---|---|---|---|---|---|---|---|
| 16 | 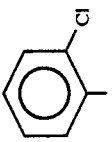 | 2-pyridyl | H | Et | 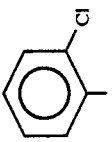 | 238-240 | 13 | 67.24 (67.48) | 4.84 4.83 | 13.78 13.89 |
| 17 | 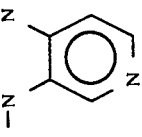 | 2-pyridyl | H | Et | 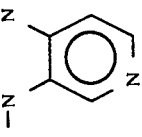 | 196-198 | 21 | 66.58 (66.40) | 5.15 5.42 | 12.93 12.91)+ |
| 18 | 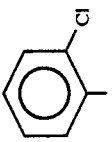 | 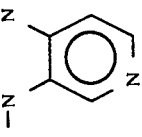 | H | Et | 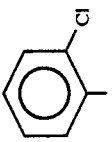 | 115-122 | 15 | | #1 | |
| 19 | 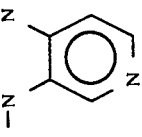 | H | H | Et |  | 158-160 | 13 | 64.25 (64.68) | 5.29 5.43 | 12.45 12.16)± |

TABLE 1-continued
| Example No. | R | R¹ | R² | R³ | X | m.p. °C. | Yield % | Analysis % (Theoretical in brackets) | | |
|---|---|---|---|---|---|---|---|---|---|---|
| | | | | | | | | C | H | N |
| 20 | 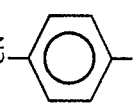 | 2-pyridyl | H | Et | 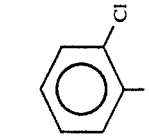 | 246–250 | 5 | | | |
| 21 | 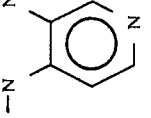 | 2-pyridyl | H | Et | 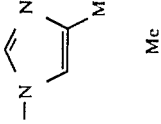 | 221–225 | 14 | 67.63 (67.66) | 5.16 5.32 | 12.20 (12.33) |
| 22 | 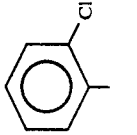 | 2-pyridyl | H | Et | 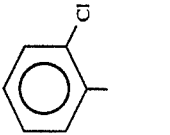 | 232–236 | 7 | 65.92 (66.13) | 4.97 5.19 | 12.38 (12.44)* |
| 23 | 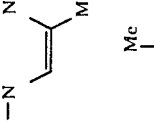 | 2-pyridyl | H | Et | 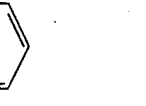 | 188–193 | 2 | 67.86 (68.09) | 5.48 5.54 | 11.99 (12.03) |
| 24 | 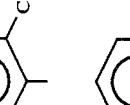 | 2-pyridyl | H | Et |  | 229–234 | 15 | 66.68 (66.81) | 5.24 5.22 | 12.48 (12.25)++ |
| 25 | 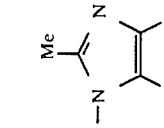 | 2-pyridyl | H | Et |  | 188–192 | 9 | 69.83 (70.14) | 5.35 5.17 | 9.96 9.91 |

TABLE 1-continued

| Example No. | R | R¹ | R² | R³ | X | m.p. °C. | Yield % | Analysis % (Theoretical in brackets) C | H | N |
|---|---|---|---|---|---|---|---|---|---|---|
| 26 | 2-chlorophenyl | 2-pyridyl | H | Et | 2,6-dimethylpyridin-3-yl | 231–234 | 2 | 69.48 (69.44) | 5.32 5.48 | 9.42 9.53)* |
| 27 | 2-chlorophenyl | 2-pyridyl | H | 2-chlorobenzyl | 2-methylimidazo[4,5-b]pyridin-3-yl | 181–183 | 46 | 65.53 (65.92) | 4.30 4.40 | 11.52 11.83)* |
| 28 | 2,3-methylenedioxyphenyl | 2-methylpyridin-3-yl | H | Et | 2-methylimidazo[4,5-b]pyridin-3-yl | 195–199° | 8± | 66.05 (65.98) | 4.89 5.14 | 12.77 13.09)φ |

*Calculated for hemihydrate;
‡Calculated for ⅓ EtOAc, ⅓ H₂O solvate;
Calculated for ⅓ isopropyl alcohol ⅓ H₂O solvate;
ΔCalculated for ⅓ H₂O;
+Calculated as ⅓ EtOAc;
++Calculated as hydrate;
¹H NMR (CDCl₃) for 1:1 mixture of diastereoisomers, 0.96(3H, t, J 7Hz), 0.97(3H, t, J 7Hz), 1.44(2H, d, J 7Hz), 1.45(2H, d, J 7Hz), 2.26(3H, s), 2.34(3H, s), 2.61(6H, s), 3.90(4H, m), 5.08(2H, m), 5.45(1H, s), 5.48(1H, s), 5.74(1H, s), 5.76(1H, s), 6.03(2H, m), 7.03–7.69(32H, complex), 8.39(2H, d, J 7Hz), 9.09(2H, s).
²H NMR (CDCl₃) 1.00(3H, t, J 7Hz), 2.47(3H, s), 2.61(3H, s), 3.97(2H, m), 5.23(1H, s), 6.42(2H, s), 7.03(1H, d, J 5Hz), 7.10(1H, d, J 6Hz), 7.42(2H, d, J 7Hz), 7.60(2H, d, J 7Hz), 7.66(4H, m), 7.90(1H, s), 8.19(1H, d, J 7Hz), 8.24(1H, d, J 6Hz), 8.29(1H, d, J 5Hz), 9.04(1H, s).
**¹H NMR (CDCl₃): 1.00(3H, t, J 7Hz), 2.31(3H, s), 3.93(2H, m), 5.63(1H, s), 5.99(1H, s), 7.02(1H, dd, J 6 and 7Hz), 7.21(2H, s), 7.28–7.37(3H, m), 7.51(2H, d, J 9Hz), 7.63(1H, m), 7.63(2H, d, J 9Hz), 8.15(2H, m), 8.28(1H, m), 8.55(1H, d, J 6Hz), 9.31(1H, br s).
± Compound was isolated as the covalent hydrate from the Hantzsch reaction and was converted to the dihydropyridine by heating under reflux in toluene in the presence of para-toluenesulphonic acid.
φCalculated as 5/4 H₂O.

EXAMPLE 29

4-(2-Chlorophenyl)-1,4-dihydro-2-[4-(3,5-dimethyl-1,2,4-triazol-1-yl)phenyl]-3-ethoxycarbonyl-6-methyl-5-[N-(2-pyridyl)carbamoyl]pyridine (a) Ethyl 2-[-(3,5-dimethyl-1,2,4-triazol-1-yl)benzoyl]-3-(2'-chlorophenyl)propenoate A mixture of ethyl 4'-(3,5-dimethyl-1,2,4-triazol-1-yl)benzoyl acetate (618 mg, 2.15 mmol), 2-chlorobenzaldehyde (302 mg, 2.15 mmol) and piperidine (2 drops) in isopropanol (10 ml) was stirred at ambient temperature for 72 hours. Volatile constitutes of the mixture were removed by evaporation and the residue purified by flash chromatography (eluting with ethyl acetate) to produce the title compound (600 mg, 68% yield).

(b) 4-(2-Chlorophenyl)-1,4-dihydro-2-[4-(3,5-dimethyl-1,2,4-triazol-1-yl)phenyl]-3-ethoxycarbonyl-6-methyl-5-[N-(2-pyridyl)carbamoyl]pyridine A mixture of the product from step (a) (566 mg, 1.38 mol) and N-(2-pyridyl)-3-aminocrotonamide (245 mg, 1.38 mmol) in ethanol (10 ml) was heated at reflux under nitrogen for 8 hours. The solvent was removed and the residue purified by flash chromatography (eluting with 2% diethylamine in ethyl acetate) to afford the title compound (50 mg, 6%) as a white solid, m.p. 130° C.

Analysis %: Found: C,63.36; H,5.43; N,13.96. Calculated: C,63.42; H,50.1; N,14.32.

The compound of Example 1 was also made by this method, using ethyl 4'-(2-methylimidazo[4,5-c]pyrid-1-yl)benzoyl acetate instead of ethyl 4'-(3,5-dimethyl-1,2,4-triazol-1-yl)benzoyl acetate. The analysis of the product was identical to that given in Example 1.

EXAMPLE 30

4-(2-Chlorophenyl)-1,4-dihydro-3-ethoxycarbonyl-6-methyl-2-[4-(4-methyloxazol-5-yl)phenyl]-5-[N-(2-pyridyl)carbamoyl]pyridine A mixture of ethyl 4'-(4-methyloxazol-5-yl)benzoyl acetate (260 mg, 1.0 mmol), N-(2-pyridyl)-3-aminocrotonamide, (160 mg, 1.1 mmol) and 2-chlorobenzaldehyde (160 mg, 1.1 mmol) in ethanol (10 ml) containing 1 drop of acetic acid was heated under nitrogen at reflux for 16 hours. The solution was allowed to cool, and all volatile materials evaporated under reduced pressure. The residue was purified by chromatography on silica gel (elution with ethyl acetate) to yield a pale yellow oil. Trituration with anhydrous diethyl ether afforded the title compound as a white solid (24 mg, 5%), m.p. 176°–179° C.

Analysis %: Found: C,66.56; H,5.22; N,9.29. Calculated (for hemietherate): C,66.90; H,5.42; N,9.46.

EXAMPLES 31–33

Further compounds of the following formula were prepared in accordance with the method of Example 30 using 2-chlorobenzaldehyde and the appropriate 4'-substituted benzoylacetate.

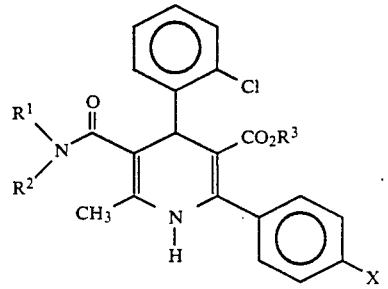

The compounds are shown in Table 2.

TABLE 2

| Example No. | R$^1$ | R$^2$ | R$^3$ | X | m.p. °C. | Yield (%) | Analysis % (Theoretical in brackets) C | H | N |
|---|---|---|---|---|---|---|---|---|---|
| 31 | 2-pyridyl | H | Et | Me-thiazolyl-Me | 215 (diffuse) | 8 | 64.82 (64.69 (hemihydrate) | 4.83 5.01 | 9.30 9.43) |
| 32 | 2-pyridyl | H | Et | Me-imidazo-thienyl | 164–166 | 6 | 64.36 (64.80 (hemietherate) | 5.21 5.14 | 10.74 10.82) |
| 33 | 2-pyridyl | H | Et | Me-thiazolyl | 193–200 | 6 | 65.02 (65.2 | 4.83 4.76 | 9.62 9.81) | a) (±)-4-(2-Chlorophenyl)-5-(2-cyanoethoxycarbonyl)-1,4-dihydro-3-ethoxycarbonyl-6-methyl-2-[4-(2-methylimidazo[4,5-c]pyrid-1-yl]phenyl)pyridine A mixture of ethyl 4'-(2-methylimidazo[4,5-c]pyrid-1-yl)benzoylacetate (7.50 gm, 23.1 mmol), 2-chlorobenzaldehyde (3.255 g, 23.1 mmol) and 2-cyanoethyl 3-aminobut-2-enoate (3.557 g, 23.1 mmol) in ethanol (60 ml) were reacted together as described in Example 1. Purification of the crude product by flash chromatography (eluting with ethyl acetate/diethylamine, 19:1), followed by trituration with ether gave the title compound as an off-white solid, (5.875 g, 44%), mp 177°–179° C.

Analysis %: Found: C,65.59; H,4.81; N,11.89. $C_{32}H_{28}ClN_5O_4$ requires: C,66.03; H,4.85; N,12.03%.

b) Resolution via the salt with 4-(2,4-dichlorophenyl)-5,5-dimethyl-2-hydroxy-1,3,2-dioxaphosphorinane-2-oxide A solution of the (±)-cyanoethyl ester prepared as above (2.340 g, 4.02 mmol) in 20 ml of hot methanol was treated with (−)-4-(2,4-dichlorophenyl)-5,5-dimethyl-2-hydroxy-1,3,2-dioxaphosphorinane-2-oxide (W. den Hoeve, H. Wynberg, *J. Org. Chem.*, (1985), 50, 4508) (1.250 g, 4.02 mmol) to form a solution of the diastereomeric salts. The solvent was evaporated and crystallisation was induced by triturating with ethyl acetate and cooling.

The resulting salts were recrystallised from methanol/toluene to give the (−)-cyanoethyl ester salt (207 mg). The mother liquors were concentrated under reduced pressure and recrystallised from dichloromethane/ethyl acetate to give a further 350 mg of the (−)-cyanoethyl ester salt, m.p. 141°–144° C., $[\alpha]_{436}^{25} = -36.9°$ (c=0.52, ethanol).

$^1$H NMR (500 Mhz, CDCl$_3$) showed that the diastereomeric ratio was 92%.

Analysis %: Found: C,56.91; H,4.70; N,7.72. C$_{43}$H$_{41}$Cl$_3$N$_5$O$_8$P.H$_2$O requires: C,56.68; H,4.76; N,7.69%.

Treatment of this salt with base (Na$_2$CO$_3$) and extraction with dichloromethane gave the (−)-cyanoethyl ester free base (271 mg). m.p. 177°–179° C. (EtOAc), $[\alpha]_{589}^{25} = -38.2°$ (c=0.28, ethanol).

Analysis %: Found: C,65.75; H,4.86; N,12.02. C$_{32}$H$_{28}$ClN$_5$O$_4$ requires: C,66.03; H,4.85; N,12.03%.

In a similar manner, the (±)-cyanoethyl ester (3.492 g, 6.0 mmol) was treated with (+)-4-(2,4-dichlorophenyl)-5,5-dimethyl-2-hydroxy-1,3,2-dioxaphosphorinane-2-oxide (1.866 g, 6.0 mmol), and the resulting salts were recrystallised from methanol/toluene and then dichloromethane/ethyl acetate to give the optically pure (+)-cyanoethyl ester salt (2.30 g). The salt was decomposed as described above to yield the (+)-cyanoethyl ester free base (735 mg), after recrystallisation from ethyl acetate, m.p. 177°–179° C. $[\alpha]_{589}^{25} = +38.9°$ (c=0.27, ethanol).

Analysis %: Found: C,66.02; H,4.94; N,12.20.

(c) (−)-4-(2-Chlorophenyl)-1,4-dihydro-3-ethoxycarbonyl-6-methyl-2-[4-(2-methylimidazo[4,5-c]pyrid-1-yl)phenyl]pyridine-5-carboxylic acid A mixture of the (−)-cyanoethyl ester from (b), above, (271 mg, 0.566 mmol) and aqueous sodium hydroxide (2.54 ml, 0.55M, 1.40 mmol) in dioxane (7.5 ml) was stirred at room temperature under nitrogen for 1 hour. Hydrochloric acid (1.40 ml, 1M, 1.40 mmol) was added dropwise, and the mixture was concentrated under reduced pressure. The resulting yellow solid was suspended in water, filtered off, and dried in vacuo, to give the title compound, (200 mg, 81%).

$^1$H NMR (300 MHz, DMSO-d$_6$) 0.8 (3H, t, J 7 Hz), 2.28 (3H, s), 2.50 (3H, s), 2.71 (2H, q, J 7 Hz), 5.37 (1H, s), 7.11 (1H, d, J 6 Hz), 7.15 (1H, m), 7.28 (2H, m), 7.49 (1H, m), 7.53 (2H, d, J 8 Hz), 7.63 (2H, d, J 8 Hz), 8.34 (1H, d, J 6 Hz), 8.93 (1H, s), 9.09 (1H, s).

(+)-4-(2-Chlorophenyl)-1,4-dihydro-3-ethoxycarbonyl-6-methyl-2-[4-(2-methylimidazo[4,5-c]pyrid-1-yl]phenyl)pyridine-5-carboxylic acid The (+)-cyanoethyl ester from (b), above, (531 mg, 0.91 mmol) was converted into the (+)-5-carboxylic acid by the method described above for the (−)-5-carboxylic acid. The product was a yellow solid (340 mg, 71%), $[\alpha]_{589}^{25} = +96.9°$ (c=0.295, ethanol).

(d) (+)-4-(2-Chlorophenyl)-1,4-dihydro-3-ethoxycarbonyl-6-methyl-2-[4-(2-methylimidazo[4,5-c]pyrid-1-yl]phenyl)-5-(N-[2-pyridyl]carbamoyl)pyridine The (−)-5-carboxylic acid (200 mg, 0.378 mmol), as prepared above, was suspended in dry dichloromethane (10 ml) under nitrogen at room temperature. 4-(N,N-dimethylamino)pyridine (115 mg, 0.945 mmol) was added, followed by 2,4,6-tri-isopropylbenzenesulphonyl chloride (286 mg, 0.945 mmol), and the resulting mixture was stirred at room temperature for 2½ hours to form a yellow solution. 2-Aminopyridine (355 mg, 3.78 mmol) was added, and the mixture was stirred for a further 4½ hours. The solution was concentrated under reduced pressure, dissolved in 0.1N aqueous hydrochloric acid, and washed with ether (30 ml). The aqueous solution was rendered basic by the addition of saturated aqueous bicarbonate, and the product was extracted into dichloromethane (4×30 ml). The extracts were combined, dried (MgSO$_4$), concentrated under reduced pressure and purified by flash chromatography (eluting with ethyl acetate:diethylamine, 19:1) to give a yellow gum, (105 mg). This material was suspended in ether, sonicated to form a powder, which was filtered off and dried in vacuo, m.p. 223°–225° C. $[\alpha]_{589}^{25} = +62.0°$ (c=0.25, ethanol).

$^1$H NMR (300 MHz, CDCl$_3$) 1.02 (3H, t, J 7 Hz), 2.32 (3H, s), 2.63 (3H, s), 3.94 (2H, q, J 7 Hz), 5.65 (1H, s), 5.94 (1H, br s), 7.03 (1H, dd, J 5 and 7 Hz), 7.15 (1H, d, J 6 Hz), 7.20 (1H, t, J 8 Hz), 7.33 (2H, m), 7.45 (2H, d, J 8 Hz), 7.68 (4H, m), 8.09 (1H, br s), 8.19 (1H, d, J 8 Hz), 8.29 (1H, d, J 5 Hz), 8.38 (1H, d, J 6 Hz), 9.09 (1H, s).

By the same method, the (+)-5-carboxylic acid (250 mg, 0.473 mmol) was converted into the (−)-5-[N-(2-pyridyl]amide (76 mg). m.p. 217°–219° C., $[\alpha]_{589}^{25} = -55.3°$ (c=0.215, ethanol).

EXAMPLE 35

4-(2-Chlorophenyl)-1,4-dihydro-3-ethoxycarbonyl-6-methyl-2-[2-(2-methylimidazo[4,5-c]pyrid-1-yl)pyrid-5-yl]-5-[N-(2-pyridyl)carbamoyl]pyridine A solution of ethyl 2-(2-methylimidazo[4,5-c]pyrid-1-yl)pyrid-5-oylacetate (324 mg, 1.0 mmol), 3-amino-N-(2-pyridyl)but-2-enamide (178 mg, 1.0 mmol) and 2-chlorobenzaldehyde (140 mg, 1.0 mmol) in ethanol (4 ml) was heated under reflux for 5 hours under nitrogen. The solution was cooled and concentrated under reduced pressure. The residue was purified by flash chromatography (eluting with ethyl acetate:methanol, 6:1), followed by sonication of a suspension of the eluted product in ether/ethyl acetate, 3:1 for 45 minutes. The off-white solid product was filtered off and dried in vacuo to give the title compound, 140 mg (23%), m.p. 242°–3° C.

Analysis %: Found: C,64.11; H,4.56; N,15.52. C$_{33}$H$_{28}$ClN$_7$O$_3$.¾ H$_2$O requires: C,63.96; H,4.79; N,15.82%.

The following Preparations relate to intermediates useful in preparing compounds of formula (I).

PREPARATION 1

Ethyl 4'-(2-methylbenzimidazol-1-yl)benzoylacetate

A suspension of activated zinc dust (994 mg, 15.2 mmol) in dry THF (10 ml) under nitrogen was sonicated for 10 minutes, then three drops of ethyl bromoacetate were added. The mixture was heated under reflux for 10 minutes, and then 1-(4-cyanophenyl)-2- methylbenzimidazole (708 mg, 3.04 mmol) was added in one portion. A solution of ethyl bromoacetate (1.35 ml, 12.1 mmol) in dry THF (4 ml) was added dropwise at reflux over 1 hour, and after a further 10 minutes, the mixture was cooled to room temperature and diluted with THF (19.5 ml). 50% Aqueous potassium carbonate (4 ml) was added, and the mixture was stirred vigorously for 30 minutes. The organic solution was filtered through Arbocel (Trade Mark) filter aid, and the inorganic salts and filter pad were washed with THF (90 ml). Dilute hydrochloric acid (10 ml) was added to the combined organic solutions and the biphasic mixture was stirred at room temperature for 14 hours. The mixture was neutralised with saturated aqueous sodium bicarbonate and concentrated under reduced pressure. The residue was partitioned between brine and dichloromethane, the organic layer was dried (MgSO$_4$) and concentrated to give a yellow oil. Purification of the crude product by flash chromatography (Et$_2$O/EtOAc, 1:1) gave the title compound (526 mg), as a pale yellow solid.

$^1$HNMR (CDCl$_3$): 1.33 (3H, t, J 7 Hz), 2.59 (3H, s), 4.1 (2H, s), 4.29 (2H, q, J 7 Hz), 7.15-7.35 (3H, m), 7.56 (2H, d, J 9 Hz), 7.79 (1H, d, J 8 Hz), 8.20 (2H, d, J 9 Hz).

PREPARATIONS 2-20

Further keto esters of formula (III) were prepared in accordance with the general method of Preparation 1 from the corresponding nitriles. The hydrolysis step, however, involved stirring a biphasic mixture of a solution of the crude product in dichloromethane with 20% aqueous trifluoroacetic acid at room temperature for 15 to 20 minutes.

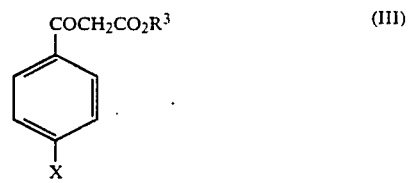

(III)

The compounds are shown in Table 3.

TABLE 3

| Preparation No. | R$^3$ | X | $^1$HNMR(CDCl$_3$) |
|---|---|---|---|
| 2 | Et | Me-C(=N-)(N-) fused pyridine (imidazo[4,5-b]pyridine) | 1.32(3H, t, J 6Hz), 2.61(3H, s), 4.09(2H, s), 4.28 (2H, q, J 6Hz), 7.16(1H, d, J 6Hz), 7.55(2H, d, J 9Hz), 8.23(2H, d, J 9Hz), 8.46(1H, d, J 6Hz), 9.09 (1H, s). |
| 3 | Et | CF$_3$-C(=N-)(N-) fused pyridine | 1.29(3H, t, J 7Hz), 4.11(2H, s), 4.26(2H, q J 7Hz), 7.21(1H, d, J 5Hz), 7.60(2H, d, J 8Hz), 8.22 (2H, d, J 8Hz), 8.59(1H, d, J 5Hz), 9.34(1H, s). |
| 4 | Et | (CH$_2$)$_3$CH$_3$-C(=N-)(N-) fused pyridine | 0.90(3H, t, J 6Hz), 1.32(3H, t, J 6Hz), 1.29-1.40 (2H, m), 1.81(2H, m), 2.84(2H, t, J 7Hz), 4.09(2H, s), 4.28(2H, q, J 6Hz), 7.09(1H, d, J 4Hz), 7.53 (2H, d, J 7Hz), 8.22(2H, d, J 7Hz), 8.41(1H, d, J 4Hz), 9.11(1H, s). |
| 5 | Et | Me-C(=N-)(N-) fused pyrazine | 1.34(3H, t, J 6Hz), 2.64(3H, s) 4.08(2H, s), 4.29 (2H, q, J 6Hz), 7.31(1H, m), 7.65(2H, d, J 9Hz), 8.06(1H, d, J 7Hz), 8.22(2H, d, J 9Hz), 8.35(1H, d, J 4Hz). |
| 6 | Et | Me-C(=N-)(N-) with N-Me triazole | 1.31(3H, t, J 6Hz), 2.31(6H, s), 4.08(2H, s), 4.29 (2H, q, J 6Hz), 7.39(2H, d, J 8Hz), 8.17(2H, d, J 8Hz). |

TABLE 3-continued

| Preparation No. | R³ | X | ¹HNMR(CDCl₃) |
|---|---|---|---|
| 7 | Et | 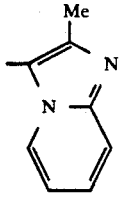 | 1.34(3H, t, J 7Hz), 2.56(3H, s), 4.08(2H, s), 4.30 (2H, q, J 7Hz), 6.82(1H, t, J 6Hz), 7.25(1H, t, J 6Hz), 7.65(1H, d, J 6Hz), 7.66(2H, d, J 8Hz), 8.14 (2H, d, J 8Hz), 8.22(1H, d, J 6Hz). |
| 8 | Et | 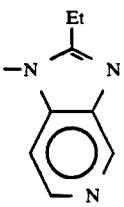 | 1.16(3H, t, J 7Hz), 1.28(3H, t, J 7Hz), 2.74(2H, q, J 7Hz), 3.98(2H, s), 4.13(2H, q, J 7Hz), 6.99(1H, d, J 7Hz), 7.45(2H, d, J 8Hz), 8.11(2H, d, J 8Hz), 8.23(1H, d, J 7Hz), 8.94(1H, s). |
| 9 | Et | 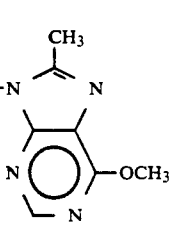 | 1.33(3H, t, J 7Hz), 2.62(3H, s), 4.08(2H, s), 4.25 (3H, s), 4.28(2H, q, J 7Hz), 7.61(2H, d, J 8Hz), 8.22(2H, d, J 8Hz), 8.53(1H, s). |
| 10 | Et | 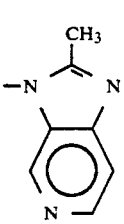 | 1.30(3H, t, J 7Hz), 2.62(3H, s), 4.11(2H, s), 4.29 (2H, q, J 7Hz), 7.71(1H, d, J 6Hz), 7.99(2H, d, J 8Hz), 8.25(2H, d, J 8Hz), 8.52(1H, d, J 6Hz), 8.60 (1H, s). |
| 11 | Et | 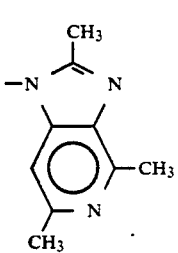 | 1.36(3H, t, J 6Hz), 2.59(3H, s), 2.62(3H, s), 2.90 (3H, s), 4.09(2H, s), 4.19(2H, q, J 6Hz), 7.55(2H, d, J 9Hz), 7.97(2H, d, J 9Hz), 8.21(1H, s). |
| 12 | Et | 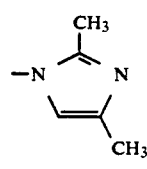 | 1.30(3H, t, J=6Hz), 2.27 and 2.41(each 3H, s), 4.05(2H, s), 4.25(2H, q, J=6Hz), 6.80(1H, s), 7.44 and 8.10(each 2H, d, J=9Hz). |
| 13 | Et | 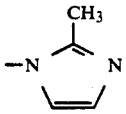 | 1.30(3H, t, J=6Hz), 2.43(3H, s) 4.06 (2H, s), 4.25(2H, q, J=6Hz), 7.08(2H, d, J=2Hz), 7.47 and 8.11(each 2H, d, J=9Hz). |
| 14 | Et | 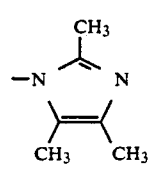 | 1.30(3H, t, J=6Hz), 1.97, 2.20 and 2.25 (each 3H, s), 4.05(2H, s), 4.25(2H, q, J=6Hz) 7.34 and 8.13(each 2H, d, J=9Hz). |

TABLE 3-continued

| Preparation No. | R³ | X | ¹HNMR(CDCl₃) |
|---|---|---|---|
| 15 | Et | 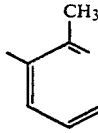 | 1.30(3H, t, J=6Hz), 2.54(3H, s), 4.06 (2H, s) 4.25(2H, q, J=6Hz), 7.25(1H, m), 7.45(3H, m), 8.08(2H, d, J=9Hz), 8.67(1H, m). |
| 16 | Et | 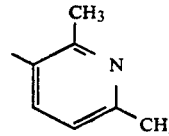 | 1.30(3H, t, J=6Hz), 2.52 and 2.62(each 3H, s), 4.05(2H, s), 4.25(2H, q, J=6Hz), 7.11(1H, d, 6Hz), 7.45(3H, m), 8.08(2H, d, J=9Hz). |
| 17 | Et | 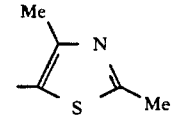 | 1.32(3H, m), 2.52 and 2.74(each 3H, s), 4.02(2H, s), 4.27(2H, m), 7.53 and 8.01(each 2H, d, J=8Hz). |
| 18 | Et | 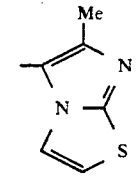 | 1.32(3H, t, J=7.5 Hz), 2.52(3H, s), 4.03(2H, s) 4.28(2H, q, J=7.5 Hz), 6.91 and 7.33(each 1H, d, J=4Hz), 7.58 and 8.09(each 2H, d, J=9.5 Hz). |
| 19 | Et | 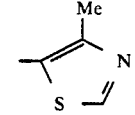 | 1.32(3H, t, J=7.5 Hz), 2.63(3H, s), 4.03(2H, s), 4.27(2H, q, J=7.5 Hz), 7.61 and 8.04(each 2H, d, J=8Hz) and 8.77(1H, s). |
| 20 | Et | 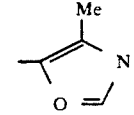 | m.p. 80–82° C. not characterised further. |

Keto esters have 5–30% enol form in CDCl₃ and spectroscopic data are reported for the keto form.

PREPARATION 21

Ethyl 4-(4-methylimidazol-1-yl)benzoylacetate (a) 4'-(4-Methylimidazol-1-yl)acetophenone A mixture of 4'-fluoroacetophenone (13.8 g, 100 mmol), 4-methylimidazole (8.2 g, 100 ml) and potassium carbonate (20.7 g, 150 mmol) in dry dimethylformamide (190 ml) was heated at 150° C. for 23 hours. Most of the solvent was evaporated at reduced pressure and the residue was partitioned between ethyl acetate and brine. The organic layer was washed (3×) with brine, dried (magnesium sulphate) and evaporated to leave a sticky solid which was purified by flash chromatography (eluting 5% diethylamine in ethylacetate). Recrystallization from ethyl acetate/hexane afforded the title compound (yield 4 g, 20%), m.p. 100° C.

(b) Title ketoester

The product of (a) (2 g, 10 mmol) was slowly added to a refluxing suspension of sodium hydride (0.44 g of a 60% dispersion in mineral oil—washed with dry hexane) in diethyl carbonate (12 ml). After heating at reflux for 1 hour, a further portion of sodium hydride was added (500 mg) and reflux was resumed for two hours. Excess sodium hydride was destroyed by addition of ethanol and the mixture was evaporated to dryness. The residue was dissolved in the minimum quantity of 2M hydrochloric acid, then partitioned between ethyl acetate and saturated aqueous sodium bicarbonate. The organic extract was dried (magnesium sulphate) and evaporated to a gum. Flash chromatography (eluting ethyl acetate) afforded the title compound as a white solid (yield 400 mg), 15%).

¹HNMR (CDCl₃): 1.30 (3H, t, J=6 Hz), 2.33 (3H, s), 4.05 (2H, s), 4.25 (2H, q, J=6 Hz), 7.11 (1H, s), 7.52 (2H, d, J=9 Hz); 7.90 (1H, s), 8.11 (2H, d, J=9 Hz).

PREPARATION 22

Ethyl 4-(3,5-dimethyl-1,2,4-triazol-1-yl)benzoylacetate

The procedure of Preparation 21 was followed but using the appropriate amount of 3,5-dimethyl-1,2,4-triazole instead of 4-methylimidazole. Step (a) produced 4'-(3,5-dimethyl-1,2,4-triazol-1-yl)acetophenone in a yield of 42%. Step (b) produced ethyl 4-(3,5-dimethyl-1,2,4-triazol-1-yl)benzoyl acetate in a yield of 63%.

¹HNMR (CDCl₃) of title ketoester: 1.30 (3H, t, J=Hz), 2.47 and 2.60 (each 3H, s), 4.04 (2H, s), 4.25 (2H, q, J=Hz), 7.66 and 8.11 (each 2H, d, J=9 Hz).

PREPARATION 23

Ethyl 4'-(1-Benzimidazolyl)benzoylacetate (a) 4'-(1-benzimidazoly)acetophenone

A mixture of p-bromoacetophenone (3.98 g, 20 mmol), benzimidazole (4.72 g, 40 mmol), copper bronze (1.27 g, 20 mmol), anhydrous potassium carbonate (5.52 g, 40 mmol) and cuprous bromide (290 mg, 2 mmol) in dry N-methylpyrrolidinone (60 ml) was heated under nitrogen at 160° C. for 8 hours. Most of the solvent was removed by distillation under reduced pressure and the residue was diluted with dichloromethane (500 ml) and 2N sodium hydroxide (200 ml). The organic layer was washed with water (300 ml), dried (MgSO$_4$) and concentrated to give a dark brown oil. Purification by flash chromatography (eluting with ethyl acetate gave 4'-(1-benzimidazolyl)acetophenone, 3.085 g as a pale yellow solid, m.p. 133°–135° C.

$^1$HNMR (CDCl$_3$): 2.73 (3H, s), 7.46 (2H, m), 7.65 (1H, m), 7.69 (2H, d, J 8 Hz), 7.94 (1H, m), 8.21 (1H, s), 8.23 (2H, d, J 8 Hz).

(b) Ethyl 4'-(1-Benzimidazolyl)benzoylacetate

The title compound was prepared by an adaptation of the method of U.S. Pat. No. 4,353,905. Sodium hydride (132 mg, 80% dispersion in oil, 4.4 mmol) was washed with dry pentane and suspended in dry THF (10 ml) under nitrogen and a solution of 4'-(1-benzimidazolyl)acetophenone (944 mg, 4.0 mmol) in dry THF (20 ml) was added dropwise. The mixture was stirred at room temperature for 1 hour and diethyl carbonate (1.21 ml, 10 mmol) was added. The mixture was refluxed for 18 hours, cooled and filtered. The solid was suspended in water, acidified with acetic acid and extracted with dichloromethane. The extracts were dried (MgSO$_4$) and concentrated. Purification of the residue by flash chromatography (eluting with ethyl acetate:hexane, 4:1) gave ethyl 4'-(1-benzimidazolyl)benzoylacetate, 449 mg as a colourless solid, m.p. 69°–71° C.

$^1$HNMR (CDCl$_3$) 1.32 (3H, t, J 6 Hz), 4.08 (2H, s), 4.28 (2H, q, J 6 Hz), 7.41 (2H, m), 7.63 (1H, m), 7.71 (2H, m), 7.94 (1H, m), 8.22 (3H, m).

Methyl 4'-(imidazol-1-yl)benzoylacetate was prepared by the method of U.S. Pat. No. 4,353,905.

PREPARATION 24

1-(4-Cyanophenyl)-2-methylbenzimidazole (a) N-(4-Iodophenyl)-2-nitroaniline

According to the method of V. P. Chernetskii, A. I. Kiprianov, *Zh. Obsch. Khim*, 1956, 26, 3465, a mixture of 2-fluoronitrobenzene (14.0 g, 100 mmol), p-iodo aniline (10.95 g, 50 mmol) and triethylamine (13.9 ml, 100 mmol) was heated under reflux for 42 hours. The mixture was cooled, diluted with ethyl acetate (300 ml) washed consecutively with water (100 ml), 2N sodium hydroxide (100 ml) and brine (100 ml). The organic layer was dried (MgSO$_4$), concentrated under reduced pressure and the residue was recrystallised from ethyl acetate to give N-(4-iodophenyl)-2-nitroaniline, 10.03 g, as bright orange needles, m.p. 171°–2° C.

(b) N-(4-Iodophenyl)1,2-diaminobenzene

According to the method of *Chem. Abs.*, 1962, 57, 9840a, a solution of sodium dithionite (85%, 24.74 g, 121 mmol) in water (120 ml) was added to a suspension of (4-iodophenyl)-2-nitroaniline in ethanol (500 ml). The mixture was heated under reflux for 45 minutes, cooled, treated with 300 ml of dilute aqueous ammonia, and concentrated under reduced pressure. The resulting white slurry was treated with 200 ml of dilute aqueous ammonia, filtered and washed with water (200 ml). The solid was dried in a vacuum desiccator at room temperature to give N-(4-iodophenyl)1,2-diaminobenzene, 8.91 g, which gradually darkens on exposure to light, m.p. 122°–123° C.

$^1$HNMR (CDCl$_3$) 3.81 (2H, br s), 5.21 (1H, br s), 6.54 (2H, d, J 8 Hz), 6.82 (2H, m), 7.09 (2H, m), 7.48 (2H, d, J 8 Hz).

(c) 1-(4-Iodophenyl)-2-methylbenzimidazole

Ethyl acetimidate hydrochloride (6.757 g, 54.9 mmol) was added to a suspension of N-(4-iodophenyl)-1,2-diaminobenzene (6.812 g, 22.0 mmol) in absolute ethanol (30 ml) at room temperature. After 2 hours, 50 ml of ice cold 2N aqueous sodium hydroxide was added and the product was extracted into ethyl acetate (2×100 ml). The extracts were washed with water (3×100 ml), dried (MgSO$_4$) and concentrated under reduced pressure to give 1-(4-iodophenyl)-2-methylbenzimidazole, 6.695 g as a white solid, m.p. 136°–7° C.

$^1$HNMR (CDCl$_3$): 2.55 (3H, s), 7.14 (1H, d, J 8 Hz), 7.17 (2H, d, J 8 Hz, 7.25 (1H, t, J 8 Hz), 7.31 (1H, t, J 8 Hz), 7.93 (1H, d, J 8 Hz), 7.95 (2H, d, J 8 Hz).

(d) 1-(4-Cyanophenyl)-2-methylbenzimidazole

Cuprous cyanide (8.323 g, 93 mmol) was added to a mixture of 1-(4-iodophenyl)-2-methylbenzimidazole (5.184 g, 15.5 mmol) and palladium (II) acetate (170 mg) in N,N'-dimethyl-1,4,5,6-tetrahydro-2-pyrimidone (15 ml) and the resulting solution was heated under nitrogen at 100° C. for 15 hours. The mixture was cooled, poured into saturated aqueous ammonia (150 ml) and shaken to dissolve the copper salts. The mixture was extracted with ether (3×150 ml), and the combined extracts were washed consecutively with water (3×150 ml), brine (150 ml), and then dried (MgSO$_4$) and concentrated under reduced pressure to give 1-(4-cyanophenyl)-2-methylbenzimidazole, 941 mg, as a white solid.

$^1$HNMR (CDCl$_3$): 2.58 (3H, s), 7.17 (1H, d, J 8 Hz), 7.27 (1H, t, J 8 Hz), 7.34 (1H, t, J 8 Hz), 7.58 (2H, d, J 8 Hz), 7.79 (1H, d, J 8 Hz), 7.95 (2H, d, J 8 Hz).

PREPARATION 25

4-(4-Cyanophenyl)-3,5-dimethyl-1,2,4-triazole

Hydrazine hydrate (1.64 ml, 34 mmol) was added dropwise to a solution of p-cyanothioacetanilide prepared according to *J. Pharm. Soc. Jpn.*, 1952, 72, 739 (5.43 gm, 30.9 mmol) in THF (50 ml) at room temperature. After 30 minutes, the solution was concentrated under reduced pressure and the residue treated with triethyl orthoacetate (40 ml). The mixture was heated at 80° C. for 30 minutes, cooled and the excess reagent was removed under reduced pressure. The residue was treated with ice-cold dilute aqueous ammonia (100 ml) and the product was filtered off, washed with water and dried in vacuo. The title triazole (4.85 g) was an off-white solid, m.p.>230° C.

$^1$HNMR (CDCl$_3$): 2.32 (6H, s), 7.42 (2H, d, J 8 Hz), 7.92 (2H, d, J 8 Hz).

PREPARATION 26

1-(4-Cyanophenyl)-2-methylimidazo[4,5-c]pyridine (a) N-(4-Cyanophenyl)-4-amino-3-nitropyridine According to the method of *J. C. S. Perkin Trans. I*, 1979, 135, p-cyanoaniline (6.894 g, 58.4 mmol) was added to a solution of 4-chloro-3-nitropyridine (9.26 g, 58.4 mmol) in ethanol (200 ml) and the mixture was stirred at room temperature for 18 hours. The resulting yellow suspension was poured into 500 ml of ice-cold dilute ammonia and filtered. The solid was treated with 150 ml of boiling ethanol, cooled in ice, and filtered to give. N-(4-cyanophenyl)-4-amino-3-nitropyridine, 12.15 g, as a bright yellow powder, m.p. 210°–211° C.

¹HNMR (CDCl₃): 7.15 (1H, d, J 6 Hz), 7.45 (2H, d, J 9 Hz), 7.79 (2H, d, J 9 Hz), 8.43 (1H, d, J 6 Hz), 9.36 (1H, s), 9.80 (1H, br s).

(b) 3-Amino-4-(4'-cyanophenyl)aminopyridine

According to a modification of the method of *Pharm. Helv. Acta*, 1975, 50, 188., tin dichloride dihydrate (56.4 g, 250 mmol) was added to a suspension of N-(4-cyanophenyl)-4-amino-3-nitropyridine (12.0 g, 50 mmol) in 2N aqueous hydrochloric acid (35 ml), water (150 ml) and ethanol (75 ml) and the resulting mixture was heated to reflux for 10 minutes under nitrogen. The mixture was cooled in ice, poured into ice-cold 2N aqueous sodium hydroxide (400 ml) and filtered. The creamy-coloured solid was washed with 2N aqueous sodium hydroxide and water, and then dried in a vacuum desiccator. The product, 3-amino-4-(4'-cyanophenyl)-aminopyridine, 9.31 g, gradually turns reddish brown on exposure to light and air.

¹HNMR (CDCl₃) 3.52 (2H, br s), 6.04 (1H, br s), 7.03 (2H, d, J 9 Hz), 7.59 (2H, d, J 9 Hz), 8.07 (1H, m), 8.20 (1H, s).

(c) 1-(4-Cyanophenyl)-2-methylimidazo[4,5-c]pyridine

A mixture of 3-amino-4-(4'-cyanophenyl)aminopyridine (9.31 g, 44.3 mmol), triethyl-orthoacetate (40 ml) and acetic anhydride (30 ml) was heated at reflux for 2 hours under nitrogen, cooled, then concentrated under reduced pressure. The brown residue was dissolved in 1M hydrochloric acid and washed with ethyl acetate (200 ml). The aqueous layer was rendered basic with saturated aqueous ammonia and extracted with dichloromethane (3×200 ml). The combined extracts were washed with water, dried (MgSO₄) and concentrated to give 1-(4-cyanophenyl)-2-methylimidazo[4,5-c]-pyridine, 6.5 g, as a brown solid.

¹HNMR (CDCl₃): 2.61 (3H, s), 7.13 (1H, d, J 6 Hz), 7.58 (2H, d, J 9 Hz), 7.98 (2H, d, J 9 Hz), 8.45 (1H, d, J 6 Hz), 9.11 (1H, s).

PREPARATION 27

1-(4-Cyanophenyl)-2-trifluoromethylimidazo[4,5-c]pyridine

A mixture of 3-amino-4-(4'-cyanophenyl)aminopyridine (420 mg, 2.0 mmol) (prepared as above), trifluoroacetaldehyde hydrate (232 mg, 2.0 mmol), and sodium metabisulphite (475 mg, 2.5 mmol) in N,N-dimethylacetamide (10 ml) was heated under reflux for 16 hours. After being cooled, the mixture was diluted with ethyl acetate (200 ml), washed with saturated aqueous sodium bicarbonate (50 ml) and water (5×50 ml). The organic layer was dried (MgSO₄) and concentrated under reduced pressure. The residue was purified by flash chromatography (eluting with ethyl acetate) to give 1-(4-cyanophenyl)-2-trifluoromethylimidazo[4,5-c]pyridine, 337 mg.

¹HNMR (CDCl₃): 7.17 (1H, d, J 5 Hz), 7.63 (2H, d, J 8 Hz), 7.99 (2H, d, J 8 Hz), 8.62 (1H, d, J 5 Hz), 9.35 (1H s).

PREPARATION 28

2-Butyl-1-(4-cyanophenyl)imidazo[4,5-c]pyridine

A mixture of 3-amino-4-(4'-cyanophenyl)aminopyridine (Preparation 26(b) (1.26 g, 6.0 mmol) and valeric anhydride (10 ml) was heated under nitrogen at reflux for 16 hours. The mixture was cooled, poured into 2N aqueous sodium hydroxide (100 ml) and left for 15 minutes. The solution was extracted with dichloromethane (3×70 ml), and the extracts were dried (MgSO₄) and concentrated under reduced pressure. Purification by flash chromatography (elution with ethyl acetate/methanol, 9:1) gave the title compound, 947 mg, as a brown solid.

¹HNMR (CDCl₃): 0.93 (3H, t, J 8 Hz), 1.4 (2H, p, J 8 Hz), 1.86 (2H, p, J 8 Hz), 2.84 (2H, t, J 8 Hz), 7.10 (1H, d, J 5 Hz), 7.56 (2H, d, J 8 Hz), 7.97 (2H, d, J 8 Hz), 8.46 (1H, d, J 5 Hz), 9.13 (1H, s).

PREPARATION 29

1-(4-Cyanophenyl)-2-ethylimidazo[4,5-c]pyridine

A mixture of 3-amino-4-(4'-cyanophenyl)aminopyridine (Preparation 26(b)) (2.00 g, 9.5 mmol) and propionic anhydride (12.2 ml, 95 mmol) were heated together under nitrogen at reflux for 17 hours. The resulting solution was treated with excess aqueous sodium bicarbonate and the product was extracted into dichloromethane (3×150 ml). The combined extracts were dried (MgSO₄), concentrated under reduced pressure, and the residue was purified by flash chromatography (gradient elution with ethyl acetate/methanol) to give the title compound as a brown solid (510 mg, 22%).

¹H NMR (300 MHz, CDCl₃) 1.45 (3H, t, J 7 Hz), 2.87 (2H, q, J 7 Hz), 7.10 (1H, d, J 5 Hz), 7.55 (2H, d, J 8 Hz), 7.96 (2H, d, J 8 Hz), 8.44 (1H, d, J 5 Hz), 9.13 (1H, s).

PREPARATION 30

9-(4-Cyanophenyl)-6-methoxy-8-methylpurine (a) 5-Amino-6-chloro-4-(4-cyanophenyl)aminopyrimidine A solution of 5-amino-4,6-dichloropyrimidine (7.00 g, 42.7 mmol) and 4-aminobenzonitrile (5.04 g, 42.7 mmol) in n-butanol (130 ml) was heated at reflux for 16 hours. After cooling the mixture the solid which precipitated out was filtered off, and partitioned between dichloromethane (500 ml) and saturated aqueous sodium bicarbonate. The organic phase was dried (MgSO₄) and concentrated under reduced pressure to give the title compound (6.31 g, 60%).

¹H NMR (300 MHz, MeOH-d₄) 7.72 (2H, d, J 8 Hz), 7.99 (2H, d, J 8 Hz), 8.02 (1H, s).

(b) 4-(Acetyl-[4-cyanophenyl]amino)-6-chloro-5-diacetylaminopyrimidine

A mixture of 5-amino-6-chloro-4-(4-cyanophenyl)aminopyrimidine (6.31 g, 25.7 mmol) and acetic anhydride (105 ml) was heated at 120° C. for 6 hours, and then left for 16 hours at 20° C. The excess of reagent was removed under reduced pressure, and the residue was recrystallised from methanol to give the title compound (4.62 g, 51%) as a white solid.

¹H NMR (300 MHZ, DMSO-d₆) 2.15 (3H, s), 2.38 (6H, s), 7.40 (2H, d, J 8 Hz), 7.80 (2H, d, J 8 Hz), 8.87 (1H, s).

(c) 6-Chloro-9-(4-cyanophenyl)-8-methylpurine 4-(N-Acetyl-N-[4-cyanophenyl]amino)-6-chloro-5-(N,N'-diacetylamino)pyrimidine (2.50 g, 6.73 mmol) was heated at 240° C. at 50 mmHg for 2 hours. The reaction melt was cooled and purified by flash chromatography eluting with ethyl acetate:dichloromethane, 3:1, to give the title compound (1.10 g, 61%).

(d) 9-(4-Cyanophenyl)-6-methoxy-8-methylpurine

Sodium metal (160 mg, 6.96 mmol) was allowed to react with dry methanol (5 ml) under nitrogen until evolution of hydrogen had ceased. 6-Chloro-9-(4-cyanophenyl)-8-methylpurine (1.03 g, 3.82 mmol) was added in one portion and the resulting slurry was heated under reflux for 90 minutes. The solvent was removed under reduced pressure and the residual gun was dissolved in dichloromethane (50 ml). The solution was washed with brine (20 ml), dried (MgSO$_4$) and concentrated under reduced pressure to give the title compound, (840 mg, 83%).

$^1$H NMR (300 MHz, CDCl$_3$). 2.63 (3H, s), 4.26 (3H, s), 7.63 (2H, d, J 8 Hz), 7.95 (2H, d, J 8 Hz), 8.52 (1H, s).

PREPARATION 31

3-(4-Cyanophenyl)-2-methylimidazo[4,5-c]pyridine (a) 2-Methylimidazo[4,5-c]pyridine A mixture of 3,4-diaminopyridine (20.0 g, 183 mmol) and acetic anhydride (360 ml) was heated at 100° C. for 16 hours. The excess reagent was removed under reduced pressure, and the residue was purified by flash chromatography eluting with ethyl acetate:methanol, 3:1. The product was a brown solid, (15.5 g, 64%).

$^1$H NMR (300 MHz, MeOH-d$_4$). 2.68 (3H, s), 7.58 (1H, d, J 6 Hz), 8.31 (1H, d, J 6 Hz), 8.80 (1H, s).

(b) 2-Methylimidazo[4,5-c]pyridine-N-oxide

Following the method of Chem. Pharm. Bull., 12, 866 (1964), a solution of 2-methylimidazo[4,5-c]pyridine (5.65 g, 42.5 mmol) in 30% aqueous hydrogen peroxide (15 ml) and glacial acetic acid was stirred at 60° C. for 6 days. The volatiles were removed under reduced pressure and the residue was dissolved in ethanol and treated with solid anhydrous potassium carbonate. The solid was filtered off, washed with ethanol, and the filtrate was concentrated under reduced pressure. The crude product was purified by flash chromatography eluting with 10-30% water in acetone. Fractions containing the product were concentrated under reduced pressure, redissolved in isopropanol/toluene, 1:1 (200 ml) and re-evaporated to give the title compound, as a hygroscopic solid, (2.94 g, 46%).

$^1$H NMR (300 MHz, MeOH-d$_4$) 2.69 (3H, s), 7.69 (2H, d, J 6 Hz), 8.23 (1H, d, J 6 Hz), 8.72 (1H, s).

(c) 3-(4-Cyanophenyl)-2-methylimidazo[4,5-c]pyridine

A mixture of 2-methylimidazo[4,5-c]pyridine-N-oxide (2.06 g, 13.8 mmol), 4-fluorobenzonitrile (1.67 g, 13.8 mmol), and anhydrous potassium carbonate (13.8 mmol) in dry dimethylformamide (35 ml) was heated under nitrogen at 140° C. for 16 hours. The mixture was filtered, and the filtrate was concentrated under reduced pressure to give a mixture of 1-and 3-(4-cyanophenyl)-2-methylimidazo-[4,5-c]pyridine-N-oxides.

This mixture was dissolved in glacial acetic acid (40 ml), and iron powder (1.16 g, 20.7 mmol) was added. The mixture was heated at 100° C. for 30 minutes, cooled, and filtered through Arbacel filter aid. The filtrate was concentrated under reduced pressure and the residue was taken up in dichloromethane (150 ml) and washed with saturated aqueous sodium bicarbonate. The organic phase was dried (MgSO$_4$) and concentrated under reduced pressure. The resulting crude product was purified by flash chromatography, eluting with ethyl acetate:methanol, 9:1 to give three fractions. First eluted was 3-(4-cyanophenyl)-2-methylimidazo[4,5-c]pyridine (415 mg, 13%).

$^1$H NMR (300 MHz, CDCl$_3$) 2.64 (3H, s), 7.62 (2H, d, J 8 Hz), 7.70 (1H, d, J 5 Hz), 7.98 (2H, d, J 8 Hz), 8.52 (1H, d, J 5 Hz), 8.59 (1H, s). Second eluted was a mixture of 3- and 1-(4-cyanophenyl)-2-methylimidazo[4,5-c]pyridines (410 mg, 13%) and third eluted was pure 1-(4-cyanophenyl)-2-methylimidazo[4,5-c]pyridine (350 mg, 11%).

PREPARATION 32

1-(4-Cyanophenyl)-2,4,6-trimethylimidazo[4,5-c]pyridine (a) 2,6-Dimethyl-3-nitro-4-pyridone 2,6-Dimethyl-4-pyridone (Chem. Abs., 84, 4811x, (1976)) (52.56 g, 0.427 mol) was dissolved in water (100 ml) at 50° C., and fuming nitric acid (40 ml) was added dropwise. The mixture was cooled in ice for 45 minutes, and then the pale buff crystals were filtered off, washed with a little water, and sucked dry to give 2,6-dimethyl-4-pyridone nitrate salt, (46.79 g, 59%). This material was added in portions to a mixture of fuming sulphuric acid (23 ml) and fuming nitric acid (31 ml) at room temperature, and the mixture was heated to 100° C. and held there for 5½ hours. The mixture was poured onto ice and neutralised with saturated aqueous potassium carbonate. The pale yellow solid which precipitated was filtered off and placed in a Soxhlet extractor and extracted with boiling isopropanol. The isopropanol was removed under reduced pressure to give the title compound, (26.5 g, 63%).

$^1$H NMR (300 MHz, MeOH-d$_4$) 2.38 (3H, s), 2.45 (3H, s), 6.39 (1H, s).

(b) 4-Chloro-2,6-dimethyl-3-nitropyridine

By the method of Yakugaku Zasshi, 87, 387 (1967), 2,6-dimethyl-3-nitro-4-pyridone (11.23 g, 66.8 mmol) and phosphorus oxychloride (57 ml) were heated together at reflux for 1½ hours. The excess reagent was removed under reduced pressure, and the residue dissolved in dichloromethane (150 ml). This solution was treated with dilute aqueous sodium bicarbonate until the aqueous layer was at pH7, and then the organic phase was separated, dried (MgSO$_4$) and concentrated under reduced pressure to give a pale yellow solid, (9.8 g, 79%). Caution: this compound is believed to be a powerful skin irritant.

$^1$H NMR (300 MHz, CDCl$_3$) 2.58 (3H, s), 2.61 (3H, s), 7.22 (1H, s).

(c) 4-(4-Cyanophenyl)amino-2,6-dimethyl-3-nitropyridine

A solution of 4-chloro-2,6-dimethyl-3-nitropyridine (9.80 g, 52.5 mmol) and 4-aminobenzonitrile (6.20 g, 52.5 mmol) in ethanol (160 ml) was stirred at room temperature for 16 hours. The solvent was removed under reduced pressure and the residue was dissolved in dichloromethane (200 ml), and washed with saturated aqueous sodium bicarbonate (100 ml). The organic phase was dried (MgSO$_4$) and concentrated under reduced pressure to give a gum which was crystallised by adding ether (100 ml) and sonicating for 5 minutes. The yellow solid (9.80 g, 70%) was filtered off and dried in vacuo, mp 171°-172° C.

$^1$H NMR (300 MHz, CDCl$_3$) 2.49 (3H, s), 2.76 (3H, s), 6.96 (1H, s), 7.35 (2H, d, J 8 Hz), 7.74 (2H, d, J 8 Hz), 8.69 (1H, br s).

(d) 3-Amino-4(4-cyanophenyl)amino-2,6-dimethylpyridine

A solution of 4-(4-cyanophenyl)amino-2,6-dimethyl-3-nitropyridine (5.00 g, 18.6 mmol) in a mixture of dichloromethane (20 ml) and ethanol (100 ml) was hydrogenated at 20° C. over 10% palladium on charcoal (500 mg) at 138 kPa (20 p.s.i.) for 3 hours. The catalyst was filtered off and the solvents were removed under reduced pressure to give the title compound as a brown solid (4.20 g, 94%).

$^1$H NMR (300 MHz, MeOH-d$_4$) 2.39 (3H, s), 2.62 (3H, s), 6.98 (1H, s), 7.11 (2H, d, J 8 Hz), 7.62 (2H, d, J 8 Hz).

(e) 1-(4-Cyanophenyl)-2,4,6-trimethylimidazo[4,5-c]pyridine

A mixture of 3-amino-4-(4-cyanophenyl)amino-2,6-dimethylpyridine (4.20 g, 17.6 mmol), acetic anhydride (12.6 ml) and acetic acid (12.6 ml) was stirred at 100° C. for 16 hours. The excess of reagents was removed under reduced pressure, and the residual gum was dissolved in water and the solution was rendered basic by the addition of concentrated aqueous ammonia. The white solid which precipitated was filtered off and dried in vacuo to give the title compound (4.06 g, 88%), mp 260°-262° C.

$^1$H NMR (300 MHz, CDCl$_3$) 2.60 (3H, s), 2.65 (3H, s), 2.90 (3H, s), 6.81 (1H, s), 7.55 (2H, d, J 8 Hz), 7.96 (2H, d, J 8 Hz).

Analysis %: Found: C, 73.57; H, 5.37; N, 21.53. C$_{16}$H$_{14}$N$_4$ requires: C, 73.26; H, 5.38; N, 21.36%.

PREPARATION 33

(1'S)-N-(1-Phenylethyl)-3-amino-but-2-enamide (1'S)-N-(1-phenylethyl)-3-ketobutanamide (*J. Chem. Eng. Data.*, 1954, 29, 229) (4.20 g, 20.5 mmol) was dissolved in ethanol (20 ml). Ammonia gas was then bubbled through the solution for 6 hours. The solvent was removed under reduced pressure to give the title compound as a golden brown oil (4.00 g, 95%), which could be used directly in the Hantzsch reaction without further purification.

PREPARATION 34

4-(2,4-dimethylimidazol-1-yl)benzonitrile

A mixture of 4-fluorobenzonitrile (3 g, 25 mmol), 2,4-dimethylimidazolium chloride (3 g, 25 mmol) and potassium carbonate (7.2 g, 52 mmol) in dimethylformamide (50 ml) was heated at 145° C. for 16 hours. Most of the solvent was evaporated in vacuo and the residue was partitioned between ethyl acetate and brine. The organic layer was dried (magnesium sulphate) and evaporated a yellow solid. Crystallization from hexane/ether afforded a pale-yellow solid (2.6 g, 57%).

$^1$HNMR, CDCl$_3$ (inter alia): 2.25 and 2.41 (each 3H, s), 6.78 (1H, s), 7.43 and 7.80 (each 2H, d, J=9 Hz).

PREPARATION 35

4-(2-Methylimidazol-1-yl)benzonitrile

The procedure of Preparation 34 was followed but using 25 mmol of 2-methylimidazolium chloride instead of 2,4-dimethylimidazolium chloride. The title nitrile was obtained in a 22% yield.

$^1$HNMR, CDCl$_3$ (inter alia): 2.44 (3H, s), 7.09 and 7.48 (each 2H, d, J=9 Hz), 7.84 (2H, d, J=8 Hz).

PREPARATION 36

4-(2,4,5-trimethylimidazol-1-yl)benzonitrile

The procedure of Preparation 34 was followed but using 25 mmol of 2,4,5-trimethylimidazolium chloride instead of 2,4-dimethylimidazolium chloride. The title nitrile was obtained in a 7% yield.

$^1$HNMR, CDCl$_3$ (inter alia): 1.96, 2.18 and 2.23 (each 3H, s), 7.34 and 7.84 (each 2H, d, J=9 Hz).

PREPARATION 37

3-(4-cyanophenyl)-2-methylpyridine t-Butyllithium (1.8 molar in pentane) (18.1 ml, 32.6 mmol) was added dropwise to a stirred solution of 4-bromobenzonitrile (2.81 g, 15.4 mmol) in anhydrous tetrahydrofuran (100 ml) under a nitrogen atmosphere at −60°±5° C.

After stirring for 20 minutes at this temperature a solution of dry zinc chloride (4.62 g, 33.8 mmol) in anhydrous tetrahydrofuran (55 ml) was added via a cannula and the stirred solution warmed to +10° C. over 10 minutes, whereupon tetrakis(triphenylphosphine)palladium (0.5 g, 0.43 mmol) and 3-bromo-2-methylpyridine (3.19 g, 18.5 mmol) were added. The clear, red solution was then stirred under reflux for 5.5 hours.

On cooling to ambient temperature, the reaction mixture was concentrated to ca. 50 ml under reduced pressure and the residue partitioned between methylene chloride (300 ml) and a solution of ethylene diamine tetraacetic acid disodium salt (8 g) and sodium carbonate (10 g) in water (500 ml). The organic extract was separated, dried over magnesium sulphate and concentrated to a dark oil under reduced pressure.

This oil was chromatographed on Merck 60 Kieselgel (Trade Mark), eluting with 0%→100% ether in hexane. Product-containing fractions were combined and concentrated under reduced pressure to give the title compound as an oil (0.6 g, 20%) which solidified on standing.

$^1$HNMR (CDCl$_3$), inter alia: 2.52 (3H, s), 7.26 (1H, m), 7.48 (2H, d, J=9 Hz), 7.53 (1H, m), 7.78 (2H, d, J=9 Hz), 8.58 (1H, m).

PREPARATION 38

Synthesis of 3-(4-cyanophenyl)-2,6-dimethylpyridine

A solution of 3-bromo-2,6-dimethylpyridine (5.58 g, 30 mmol) in anhydrous tetrahydrofuran (20 ml) was added to a stirred suspension of magnesium turnings (0.8 g, 33 mmol) and a single crystal of iodine in anhydrous tetrahydrofuran (15 ml) under a nitrogen atmosphere at the reflux temperature. Stirring was continued at reflux for an additional 1 hour.

On cooling to ambient temperature, a solution of dry zinc chloride (4.1 g, 30 mmol) in anhydrous tetrahydrofuran (40 ml) was added to the stirred reaction mixture via cannula, followed by addition of tetrakistriphenylphosphine palladium (0.2 g, 17 mmol) and a solution of 4-bromobenzonitrile (2.34 g, 13 mmol) in anhydrous tetrahydrofuran (5 ml). The reaction mixture was stirred at reflux for 1 hour.

On cooling to ambient temperature, the reaction mixture was partitioned between methylene chloride (200 ml) and a solution of ethylenediaminetetraacetic acid disodium salt (8 g) and sodium carbonate (10 g) in water (500 ml). The organic extract was separated, dried over magnesium sulphate and concentrated under reduced pressure to an oil.

This oil was 'flash' chromatographed on Merck 60 Kieselgel, eluting with ether:hexane:diethylamine (25:75:2). Product-containing fractions were combined and concentrated to ca. 10 ml. The ensuing crystalline precipitate was filtered, washed with ether and air-dried to give the title compound (1.2 g, 44%).

$^1$HNMR (CDCl$_3$) inter alia: 2.50 and 2.62 (each 3H, s), 7.12 and 7.43 (each 1H, d, J=8 Hz), 7.47 and 7.77 (each 2H, d, J=9 Hz).

PREPARATION 39

5-(4-Cyanophenyl)-4-methyloxazole

A stirred, two-phase mixture of formamide (0.6 ml, 15 mmol) and 4-(1-bromo-2-oxopropyl)benzonitrile (0.8 g, 3.4 mmol) was heated to 120° for 2 hours. After cooling, dichloromethane (15 ml) and saturated aqueous sodium bicarbonate (10 ml) were added, the organic phase was separated, dried (magnesium sulphate) and the solvent removed under reduced pressure to yield 0.4 g of an amorphous yellow solid. The product was purified by silica gel chromatography, eluting with dichloromethane to yield the title compound (0.29 g, 47%) as a pale yellow solid, m.p. 120°-121° C.

PREPARATION 40

5-(4-Cyanophenyl)-6-methylimidazo[2,1-b]thiazole

A solution of 4-(1-bromo-2-oxopropyl)benzonitrile (1 g, 4 mmol) in n-butanol (3 ml) was added in a single portion to a hot (110° C.), stirred solution of 2-aminothiazole in n-butanol (3 ml). After refluxing for 2 hours, triethylamine (0.5 ml, 4 mmol) was added and heating was resumed for a further 2 hours. All volatiles were evaporated and the residue was chromatographed on silica gel, eluting with ethyl acetate:hexane:diethylamine (5:14:1) to afford an off-white solid (0.34 g, 35%), m.p. 88°-91° C.

PREPARATION 41

5-(4-Cyanophenyl)-2,4-dimethylthiazole

A solution of 4-(1-bromo-2-oxopropyl)benzonitrile (0.9 g, 3.83 mmol) in toluene (2 ml) was treated with thioacetamide (0.6 g, 8 mmol) followed by pyridine (0.45 ml). The mixture was warmed to 100° C. for 1 hour, then partitioned between ethyl acetate and brine. The organic layer was dried (MgSO$_4$) and evaporated to a yellow oil. Chromatography on silica gel, eluting with 5% ether in dichloromethane, afforded a pale yellow oil which crystallised (0.52 g, 64%), m.p. 108°-110° C.

PREPARATION 42

5-(4-Cyanophenyl)-4-methylthiazole (a) 5-(4-Cyanophenyl)-4-methylthiazol-2-thiol A solution of 4-(1-bromo-2-oxopropyl)benzonitrile (4.65 g, 0.02 mol) in absolute ethanol (20 ml) was added over 10 minutes to a stirred suspension of ammonium dithiocarbamate (2.2 g, 0.02 mol) in absolute ethanol (20 ml) at ambient temperature and the reaction mixture stirred for an additional 24 hours. The reaction mixture was then diluted with H$_2$O (50 ml), the bulk of the ethanol evaporated under reduced pressure and product extracted with ethyl acetate. The organic extract was dried (MgSO$_4$), filtered and the filtrate concentrated in vacuo. Trituration of the residue with ethanol and filtration gave the title product (1.2 g, 26%).

(b) 5-(4-Cyanophenyl)-4-methylthiazole

Raney Nickel (1 g) was added to a solution of the product of (a) (1.2 g, 5 mmol) in absolute ethanol (120 ml) and the reactants heated at 80° C. in an autoclave for 18 hours. After cooling to ambient temperature, further Raney Nickel (1 g) was added to the reaction mixture and the reactants heated at 80° C. in an autoclave for an additional 6 hours. The reaction mixture was then filtered through Arbocel and the filtrate evaporated to dryness. The residue was flash chromatographed (Merck 60 Kieselgel-ethyl acetate:hexane:diethylamine, 25:75:2) to give the title product as a gum which solidified on standing (0.36 g, 35%), and was used directly in Preparation 19.

PREPARATION 43

Ethyl 2-(2-methylimidazo[4,5-c]pyrid-1-yl)pyrid-5-oyl acetate (a) 4-Chloro-1-(5-ethoxycarbonylpyrid-2-yl)-2-methylimidazo[4,5-c]pyridine 4-Chloro-2-methylimidazo[4,5-c]pyridine described in C.A. 79, 105515f but made by the method of *Chem. Pharm. Bull*, 12 (8) 866-872 (1964) (3.34 g, 20 mmol), and ethyl 6-chloronicotinate (3.71 g, 26.2 mmol) were dissolved in N,N-dimethylformamide (42 ml). Potassium carbonate (2.76 g, 20 mmol) was added and the reaction was refluxed overnight. The reaction mixture was cooled, the solvent removed under reduced pressure and the crude product purified by flash chromatography eluting with ethyl acetate. Fractions containing product were evaporated and the resulting foam triturated with ether. The solid was filtered and dried under reduced pressure yielding the title compound as a yellow solid (3.2 g, 51%).

$^1$H NMR (300 MHz, CDCl$_3$) 1.47 (3H, t, J 6 Hz), 2.84 (3H, s), 4.56 (2H, q, J 6 Hz), 7.38 (1H, d, J 4 Hz), 7.59 (1H, d, J 6 Hz), 8.25 (1H, d, J 4 Hz), 8.63 (1H, d, J 6 Hz), 9.36 (1H, s).

(b) 1-(5-Ethoxycarbonylpyrid-2-yl)-2-methylimidazo[4,5-c]pyridine

A solution of 4-chloro-1-(5-ethoxycarbonylpyrid-2-yl)-2-methylimidazo[4,5-c]pyridine in ethanol (100 ml) was hydrogenated over 30% palladium on carbon (3 g) and magnesium oxide (0.8 g) at 50 p.s.i. (345 kPa) for 30 hours. The mixture was filtered through Arbocel filter aid and the filter cake washed with boiling ethanol (6×50 ml). The filtrate was concentrated under reduced pressure yielding the title compound as a white foam, (2.75 g, 96%).

$^1$H NMR (300 MHZ, methanol-d$_4$) 1.51 (3H, t, J 6 Hz), 2.83 (3H, s), 4.53 (2H, q, J 6 Hz), 7.70 (1H, d, J 4 Hz), 7.92 (1H, d, J 6 Hz), 8.43 (1H, d, J 4 Hz), 8.72 (1H, d, J 6 Hz), 8.97 (1H, s), 9.32 (1H, s).

(c) 6-(2-Methylimidazo[4,5-c]pyrid-1-yl)pyridine-3-carboxylic acid 1-(5-Ethoxycarbonylpyrid-2-yl)-2-methylimidazo[4,5-c]pyridine (2.75 g, 9.75 mmol) was dissolved in ethanol (15 ml) and 2N aqueous sodium hydroxide (5.8 ml) was added. The mixture was stirred for 3 days at room temperature and then the solvent was removed under reduced pressure. The residue was neutralised (pH6) with dilute hydrochloric acid, and the resulting precipitate was filtered off and dried in vacuo. The title compound was obtained as a white solid (1.70 g, 69%).

$^1$H NMR (300 MHz, DMSO-d$_6$) 2.70 (3H, s), 7.58 (1H, d, J 4 Hz), 7.93 (1H, d, J 6 Hz), 8.36 (1H, d, J 4 Hz), 8.58 (1H, d, J 6 Hz), 8.96 (1H, s), 9.18 (1H, s).

(d) Ethyl 2-(2-methylimidazo[4,5-c]pyrid-1-yl)pyrid-5-oylacetate 6-(2-Methylimidazo[4,5-c]pyrid-1-yl)pyridine-3-carboxylic acid (50 mg) was suspended in dry dichloromethane (1 ml) and oxalyl chloride (29 mg) and N,N-dimethylformamide [1.5 mg] were added. The mixture was sonicated at room temperature for 1 hour yielding a suspension of 6-(2-methylimidazo[4,5-c]pyrid-1-yl)pyrid-3-oyl chloride in dichloromethane.

Ethyl potassium malonate (57 mg) was suspended in dry tetrahydrofuran (1 ml) and 2M isopropyl magnesium chloride in THF (170 μl) added. The suspension was sonicated for ½ hour giving a homogenous solution. This was added with stirring to the suspension of 6-(2-methylimidazo[4,5-c]pyrid-3-oyl chloride in dichloromethane. The mixture was stirred at room temperature for ½ hour. It was then poured into 1N hydrochloric acid, stirred for 15 minutes and adjusted to pH8 with saturated sodium bicarbonate. The aqueous phase was extracted with dichloromethane (2×10 ml), the extracts combined, dried over magnesium sulphate and the solvent removed under reduced pressure yielding the title compound as a pale red oil (40 mg, 63%) [as a 1:1 mixture of enol and keto tautomers].

$^1$HNMR CDCl$_3$: 1.40 (3H, m); 2.78 and 2.80 (3H, 2×s) 4.10 (1H, s); 4.30 (2H, m); 5.80 (½H, s); 7.40 (1H, m); 7.57 (½H, d, J=5 Hz); 7.62 (½H, d, J=5 Hz); 8.37 (½H, d, J=5 Hz); 8.42 (1H, m); 8.57 (½H, d, J=5 Hz); 9.10 (1½H, s); 9.25 (½H, s); 12.87 (½H, Br).

PREPARATION 44

5-(4-Cyanophenyl)-4-methylimidazo[1,2-a]pyridine (a) 4-(1-Bromo-2-oxopropyl)benzonitrile Bromine (5.28 g) in dichloromethane (80 ml) was added dropwise at 25° C. over 1 hour to 4-(2-oxopropyl) benzonitrile in dichloromethane (85 ml). The reaction mixture was stirred for ½ hour after the addition was complete. The mixture was washed with brine (50 ml), dried over magnesium sulphate and the solvent removed under reduced pressure to yield the title compound as a pale red oil (7.55 g, 96%).

$^1$HNMR (CDCl$_3$): 2.41 (s, 3H); 5.24 (s, 1H); 7.61 (d, J=4 Hz, 2H); 7.73 (d, J=4 Hz, 2H).

(b) 5-(4-Cyanophenyl)-4-methylimidazo[1,2-a]pyridine

A mixture of 2-aminopyridine (178 mg) and 4-(1-bromo-2-oxopropyl)benzonitrile (450 mg) were stirred in refluxing ethanol (2 ml) for 5 hours and then the ethanol was removed under reduced pressure. Dichloromethane (15 ml) and saturated aqueous sodium bicarbonate (10 ml) were added, the organic phase was separated, dried (magnesium sulphate) and the solvent removed under reduced pressure. The product was purified by flash chromatography over silica gel eluting with ethyl acetate to yield the title compound (180 mg, 41%) as a white solid.

$^1$HNMR (CDCl$_3$): 2.47 (s, 3H); 6.84 (t, J=4H, 1H); 7.25 (d, J=4 Hz, 1H); 7.62 (d, J=5 Hz, 2H); 7.86 (d, J=4 Hz, 2H); 8.17 (d, J=4 Hz, 1H).

PREPARATION 45

2-Chlorobenzyl 4'-(2-methylimidazo[4,5-c]pyrid-1-yl)Benzoylacetate

A mixture of ethyl 4'-(2-methylimidazo[4,5-c]pyrid-1-yl)benzoylacetate (320 mg, 1 mmol) and 2-chlorobenzyl alcohol (710 mg, 5 mmol) in toluene (5 ml) was heated at reflux for 20 hours. The solution was evaporated and the residue was purified by flash chromatography (elution with 10% methanol in ethyl acetate) to afford a colourless foam (300 mg, 72%) mp<40° C. Analysed for 0.5 H$_2$O.

Analysis %: Found: C,64.14; H,4.38; N,9.55. Requires: C,64.41; H,4.47; N,9.80.

PREPARATION 46

3-(4-Cyanophenyl)-2-methylimidazo[4,5-b]pyridine (a) N-(4-cyanophenyl)-2-amino-3-nitropyridine A mixture of p-cyanoaniline (2.36 g) and 2-chloro-3-nitropyridine (3.17 g) in ethanol (60 ml) was heated at reflux for 3 days. The solid which formed was filtered off, partitioned between dichloromethane (50 ml) and saturated aqueous sodium bicarbonate (30 ml). The organic layer was dried (MgSO$_4$) and concentrated to give a yellow solid which was recrystallised from ethyl acetate. Yield 2.70 g.

$^1$HNMR (CDCl$_3$) 7.03 (1H, dd, J 4 and 8 Hz), 7.69 (2H, d, J 9 Hz), 7.92 (2H, d, J 9 Hz), 8.59 (1H, d, J 4 Hz), 8.62 (1H, d, J 8 Hz), 10.39 (1H, brs).

This product was converted to 3-(4-cyanophenyl)-2-methylimidazo[4,5-b]pyridine in a manner analogous to that described above in Preparation 26 parts (b) and (c).

(b) 3-Amino-2-(4-cyanophenyl)aminopyridine $^1$HNMR (CD$_3$OD) 6.92 (1H, dd, J 4 and 8 Hz), 7.19 (1H, d, J 8 Hz), 7.45 (2H, d, J 9 Hz), 7.58 (2H, d, J 9 Hz), 7.69 (1H, d, J 4 Hz).

(c) 3-(4-Cyanophenyl)-2-methylimidazo[4,5-b]pyridine $^1$HNMR (CDCl$_3$) 2.66 (3H, s), 7.31 (1H, dd, J 5 and 8 Hz), 7.66 (2H, d, J 9 Hz), 7.94 (2H, d, J 9 Hz), 8.07 (1H, d, J 8 Hz), 8.34 (1H, d, J 5 Hz).

What is claimed is:

1. A compound of the formula (IV):

$$\begin{array}{c} R \phantom{xxxx} O \\ \phantom{x}\diagdown \phantom{xx} \| \\ \phantom{xxx} C - O - R^3 \\ H \diagup \phantom{xxx} | \\ \phantom{xxxxx} C \\ \phantom{xxx} \diagup \phantom{x} \diagdown \\ \phantom{xx} O \phantom{xxx} Y - X \end{array}$$

wherein Y is 1,4-phenylene, R is phenyl, chlorophenyl, trifluoromethoxyphenyl, difluorophenyl, cyanophenyl, fluorophenyl or methylenedioxyphenyl, R$^3$ is alkyl having one to six carbon atoms ante X is benzimidazol-1-yl or 2-methylbenzimidazol-1-yl.

* * * * *